US008633028B2

(12) United States Patent
Gross et al.

(10) Patent No.: US 8,633,028 B2
(45) Date of Patent: Jan. 21, 2014

(54) DSRNA INDUCED SPECIFIC AND NON-SPECIFIC IMMUNITY IN CRUSTACEANS AND OTHER INVERTEBRATES AND BIODELIVERY VEHICLES FOR USE THEREIN

(75) Inventors: Paul S. Gross, Charleston, SC (US); Gregory Warr, Charleston, SC (US); Robert Chapman, Charleston, SC (US); Craig Browdy, Charleston, SC (US); Javier Robalino, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 1542 days.

(21) Appl. No.: 10/883,009

(22) Filed: Jul. 2, 2004

(65) Prior Publication Data
US 2005/0080032 A1 Apr. 14, 2005

Related U.S. Application Data

(60) Provisional application No. 60/484,531, filed on Jul. 2, 2003, provisional application No. 60/498,603, filed on Aug. 29, 2003, provisional application No. 60/505,714, filed on Sep. 25, 2003, provisional application No. 60/564,295, filed on Apr. 22, 2004.

(51) Int. Cl.
*A61K 48/00* (2006.01)
*C12N 15/85* (2006.01)
*C12Q 1/68* (2006.01)

(52) U.S. Cl.
USPC .......................................... 435/455; 514/44 A

(58) Field of Classification Search
CPC ................. A61K 2039/55561; C12N 15/1131
USPC .......................................... 435/455; 514/44 A
See application file for complete search history.

(56) References Cited

U.S. PATENT DOCUMENTS

| | | | |
|---|---|---|---|
| 5,270,175 A | 12/1993 | Moll | |
| 5,977,437 A | 11/1999 | Villand et al. | |
| 6,326,193 B1 * | 12/2001 | Liu et al. | 435/320.1 |
| 6,379,968 B1 | 4/2002 | Poulsen | |
| 6,440,466 B1 * | 8/2002 | Desai et al. | 424/725 |
| 6,506,559 B1 * | 1/2003 | Fire et al. | 435/6 |
| 6,573,099 B2 | 6/2003 | Graham | |
| 7,282,564 B2 | 10/2007 | Mello et al. | |
| 7,538,095 B2 | 5/2009 | Fire et al. | |
| 7,560,438 B2 | 7/2009 | Fire et al. | |
| 7,754,697 B2 | 7/2010 | Graham et al. | |
| 2002/0164706 A1 | 11/2002 | Huang et al. | |
| 2002/0168707 A1 | 11/2002 | Graham | |
| 2003/0051263 A1 | 3/2003 | Fire et al. | |
| 2003/0055020 A1 | 3/2003 | Fire et al. | |
| 2003/0056235 A1 | 3/2003 | Fire et al. | |
| 2003/0074684 A1 | 4/2003 | Graham et al. | |
| 2003/0159161 A1 | 8/2003 | Graham et al. | |
| 2003/0203868 A1 * | 10/2003 | Bushman et al. | 514/44 |
| 2004/0064842 A1 | 4/2004 | Graham et al. | |
| 2004/0180439 A1 | 9/2004 | Graham et al. | |
| 2004/0237145 A1 | 11/2004 | Graham et al. | |
| 2004/0266005 A1 | 12/2004 | Graham et al. | |
| 2004/0266708 A1 * | 12/2004 | Diamond | 514/44 |
| 2005/0095199 A1 * | 5/2005 | Whyard et al. | 424/9.2 |
| 2005/0250208 A1 | 11/2005 | Graham et al. | |
| 2006/0014715 A1 | 1/2006 | Graham et al. | |
| 2006/0024798 A1 | 2/2006 | Mello et al. | |
| 2006/0120999 A1 | 6/2006 | Dhar et al. | |
| 2008/0050342 A1 | 2/2008 | Fire et al. | |
| 2008/0081373 A1 | 4/2008 | Fire et al. | |
| 2008/0248576 A1 | 10/2008 | Fire et al. | |
| 2009/0311786 A1 | 12/2009 | Fire et al. | |

FOREIGN PATENT DOCUMENTS

| | | | |
|---|---|---|---|
| JP | 2003506338 A | | 2/2003 |
| WO | WO 9949029 A1 | * | 9/1999 |
| WO | WO 00/73455 A1 | | 12/2000 |
| WO | WO0073455 A1 | * | 12/2000 |
| WO | WO 01/09340 A1 | | 2/2001 |
| WO | WO 02/22664 A2 | | 3/2002 |
| WO | WO 03/004644 A1 | | 1/2003 |
| WO | WO03004644 A1 | * | 1/2003 |
| WO | WO 03/028656 | | 4/2003 |
| WO | WO 2004/085645 A1 | | 10/2004 |
| WO | WO 2005/079236 A2 | | 9/2005 |

OTHER PUBLICATIONS

Huang et al. Dev Comp Immunol. Oct.-Dec. 1999;23(7-8):545-52.*
Song et al. Dev Biol Stand. 1997;90:413-21.*
International Preliminary Report on Patentability corresponding to PCT International Application No. PCT/US04/21271 dated Oct. 11, 2005.
Cereghino et al. "Applications of Yeast in Biotechnology: Protein Production and Genetic Analysis" *Current Opinion in Biotechnol.* 10:422-427 (1999).
Cereghino et al. "Heterologous Protein Expression in the Methylotrophic Yeast *Pichia pastoris*" *FEMS Microbiol. Reviews* 24:45-66 (2000).

(Continued)

*Primary Examiner* — Janet Epps-Smith
(74) *Attorney, Agent, or Firm* — Myers Bigel Sibley & Sajovec, PA

(57) ABSTRACT

Methods for inducing systemic, non-specific and/or sequence specific immune responses in invertebrates, e.g., marine invertebrates such as mollusks, porifera, ctenophora, echinodermas, marine worms, cnideria and preferably crustaceans, by the administration of at least one dsRNA, that confers immunity against a pathogen, or modulates expression of gene that affects growth, reproduction, and general health or "robustness" are provided. Also provided are methods of identifying invertebrate genes, e.g., crustacean genes, the expression of which is involved in the induction of non-specific (systemic) immune responses against pathogens. Also disclosed are preferred delivery systems and methods for stably administering at least one dsRNA to a crustacean whereby the dsRNA is administered via injection, immersion, in a feed or nutrient medium or comprised in a microorganism, e.g., yeast or microalgae, that expresses said dsRNA and is ingestible by said crustacean, e.g., a shrimp.

3 Claims, 16 Drawing Sheets

(56) References Cited

OTHER PUBLICATIONS

Figure 2A:
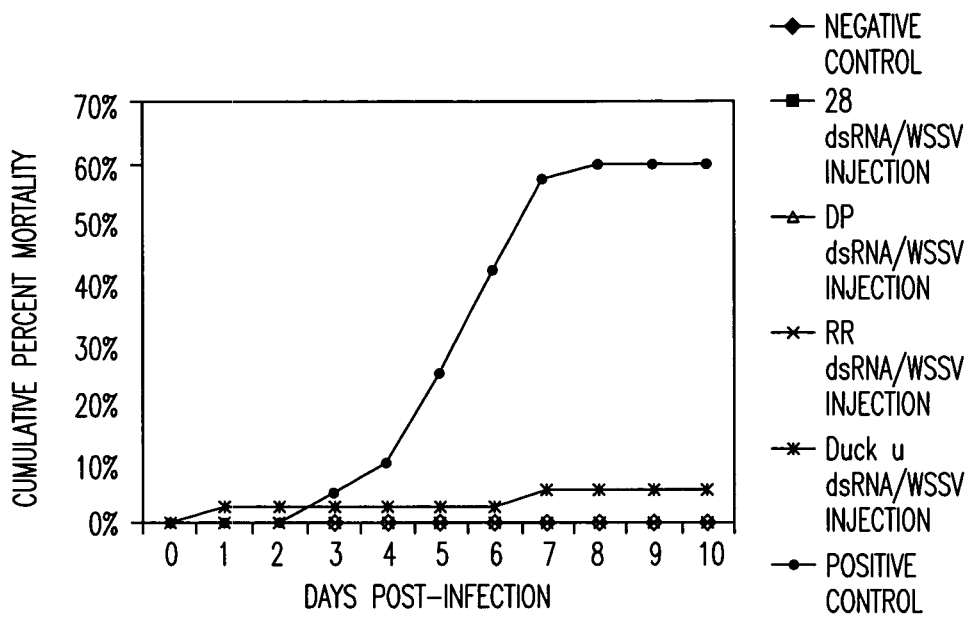

Chen et al. "Transfection of mEpo Gene to Intestinal Epithelium in vivo Mediated by Oral Delivery of Chitosan-DNA Nanoparticles" *World J. Gastroenterol.* 10(1):112-116 (2004).

De Backer et al. "An Antisense-based Functional Genomics Approach for Identification of Genes Critical for Growth of *Candida albicans*" *Nature Biotechnology* 19:235-241 (2001).

Fire et al. "Potent and Specific Genetic Interference by Double-Stranded RNA in *Caenorhabditis elegans*" *Nature* 391:806-811 (1998).

Hammond et al. "Post-Transcriptional Gene Silencing by Double-Stranded RNA" *Nature* 2:110-119 (2001).

Hannon. "RNA Interference" *Nature* 418:244-251 (2002).

Kamath et al. "Effectiveness of Specific RNA-mediated Interference Through Ingested Double-Stranded RNA in *Caenorhabditis elegans*" *Genome Biology* 2(1):research0002.1-0002.10 (2000).

Lapidot et al. "Stable Chloroplast Transformation of the Unicellular Red Alga *Porphyridium* Species" *Plant Physiology* 129:7-12 (2002).

Martinez et al. "Genetic Transformation of Astaxanthin Mutants of *Phaffia rhodozyma*" *Antonie van Leeuwenhoek* 73:147-153 (1998).

Mason et al. "Expression of Hepatits B Surface Antigen in Transgenic Plants" *Proc. Natl. Acad. Sci USA* 89:11745-11749 (1992).

Mayfield et al. "Stable Nuclear Transformation of *Chlamydomonas reinhardtii* by Using a *C. reinhardtii* Gene as the Selectable Marker" *Proc. Natl. Acad. Sci. USA* 87:2087-2091 (1990).

Mayfield et al. "Expression and Assembly of a Fully Active Antibody in Algae" *Proc. Natl. Acad. Sci. USA* 100:438-442 (2003).

McCown et al. "The Utility of siRNA Transcripts Produced by RNA Polymerase I in Down Regulating Viral Gene Expression and Replication of Negative- and Positive-Strand RNA Viruses" *Virology* 313:514-524 (2003).

Rosas et al. "Stable Expression of Antisense RNAs Targeted to the 5' Non-Coding Region Confers Heterotypic Inhibition to Foot-and-Mouth Disease Virus Infection" *Journal of General Virology* 84:393-402 (2003).

Sturino et al. "Expression of Antisense RNA Targeted Against *Streptococcus thermophilus* Bacteriophages" *Applied and Environmental Microbiology* 68(2):588-596 (2002).

Uzbekova et al. "Transgenic Rainbow Trout Expressed sGnRH-antisense RNA Under the Control of sGnRH Promoter of Atlantic Salmon" *J. of Mol. Endocrinol.* 25:337-350 (2000).

Wery et al. "High Copy Number Integration into the Ribosomal DNA of the Yeast *Phaffia rhodozyma*" *Gene* 184:89-97 (1997).

Wilson et al. "RNA Interference Blocks Gene. Expression and RNA Synthesis From Hepatitis C Replicons Propagated in Human Liver Cells" *Proc. Natl. Acad. Sci. USA* 100:2783-2788 (2003).

Xia et al. "siRNA-Mediated Gene Silencing in vitro and in vivo" *Nature Biotechnology* 20:1006-1010 (2002).

Assavalapsakul et al. "Identification and Characterization of a *Penaeus monodon* Lymphoid Cell-Expressed Receptor for the Yellow Head Virus" *Journal of Virology* 80(1):262-269 (2006).

Specification of U.S. Appl. No. 60/354,684, filed Feb. 6, 2002, entitled "Inhibition of Pathogen Replication by RNA interference".

Specification of U.S. Appl. No. 60/352,705, filed Jan. 29, 2002, entitled "Polymerase-mediated Regulation of Polynucleic Acids".

Hiu-Kwan et al. "The use of recombinant protein and RNA interference approaches to study the reproductive functions of a gonad-stimulating hormone from the shrimp *Metapenaeus ensis*" *FEBS Journal* 274:4385-4395 (2007).

Kim et al. "Protection of shrimp (*Penaeus chinensis*) against white spot syndrome virus (WSSV) challenge by double-stranded RNA" *Fish & Shellfish Immunology* 23:242-246 (2007).

Li et al. "β-integrin mediates WSSV infection" *Virology* 368:122-132 (2007).

Liu et al. "Antilipopolysaccharide Factor Interferes with White Spot Syndrome Virus Replication In Vitro and In Vivo in the Crayfish *Pacifastacus leniusculus*" *Journal of Virology* 80(21):10365-10371 (2006).

Lugo et al. "Molecular cloning and characterization of the crustacean hyperglycemic hormone cDNA from *Litopenaeus schmitti*. Functional analysis by double-stranded RNA interference technique" *FEBS Journal* 273:5669-5677 (2006).

Maningas et al. "Essential function of transglutaminase and clotting protein in shrimp immunity" *Mol. Immunol.* (2007), Online Publication Oct. 29, 2007.

Robalino et al. "Induction of Antiviral Immunity by Double-Stranded RNA in a Marine Invertebrate" *Journal of Virology* 78(19):10442-10448 (2004).

Robalino et al. "Double-Stranded RNA Induces Sequence-Specific Antiviral Silencing in Addition to Nonspecific Immunity in a Marine Shrimp: Convergence of RNA Interference and Innate Immunity in the Invertebrate Antiviral Response?" *Journal of Virology* 79(21):13561-13571 (2005).

Sarathi et al. "Silencing VP28 Gene of White Spot Syndrome Virus of Shrimp by Bacterially Expressed dsRNA" *Marine Biotechnology* (2007), Online Publicaton Oct. 27, 2007.

Tirasophon et al. "Therapeutic inhibition of yellow head virus multiplication in infected shrimps by YHV-protease dsRNA" *Antiviral Research* 74:150-155 (2007).

Tirasophon et al. "Silencing of yellow head virus replication in penaeid shrimp cells by dsRNA" *Biochemical and Biophysical Research Communications* 334:102-107 (2005).

Tiu et al. "The LvCHH-ITP gene of the shrimp (*Litopenaeus vannamei*) produces a widely expressed putative ion transport peptide (LvITP) for osmo-regulation" *Gene* 396:226-235 (2007).

Westenberg et al. "siRNA injection induces sequence-independent protection in *Penaeus monodon* against white spot syndrome virus" *Virus Research* 114:133-139 (2005).

Witteveldt et al. "Protection of *Penaeus monodon* against White Spot Syndrome Virus by Oral Vaccination" *Journal of Virology* 78(4):2057-2061 (2004).

Yodmuang et al. "YHV-protease dsRNA inhibits YHV replication in *Penaeus monodon* and prevents mortality" *Biochemical and Biophysical Research Communications* 341:351-356 (2006).

Fjose et al. "RNA Interference: Mechanisms and Applications" *Biotechnol Annu Rev* 7:31-57 (2001).

Haasnoot et al. "Inhibition of Virus Replication by RNA Interference" *Journal of Biomedical Science* 10:607-616 (Oct. 2003).

Levy and Garcia-Sastre. "The Virus Battles: IFN Induction of the Antiviral State and Mechanisms of Viral Evasion" *Cytokine & Growth Factor Reviews* 12:143-156 (2001).

Pomerantz. "RNA Interference Meets HIV-1: Will Silence be Golden?" *Nature Medicine* 8(7):659-660 (Jul. 2002).

Roignant et al. "Absence of Transitive and Systemic Pathways Allows Cell-Specific and Isoform-Specific RNAi in *Drosophila*" *RNA* 9(3):299-308 (Mar. 2003).

Tiu and Chan. "The Use of Recombinant Protein and RNA Interference Approaches to Study the Reproductive Functions of a Gonad-Stimulating Hormone from the Shrimp *Metapenaeus ensis*" *FEBS Journal* 274:4385-4395 (2007).

Timmons et al. "Inducible Systemic RNA Silencing in *Caenorhabditis elegans*" *Molecular Biology of the Cell* 14:2972-2983 (2003).

Cerutti. "RNA Interference: Traveling in the Cell and Gaining Functions?" *Trends Genet* 19(1):39-46 (2003).

Office Action and subsequent Response in corresponding Chinese Application No. 200480025135.8; Office Action dated Dec. 2009; Response filed May 2010.

Lee and Soderhall. "Early Events in Crustacean Innate Immunity" *Fish Shellfish Immunol* 12(5):421-437 (2002).

Li et al. "Interferon Antagonist Proteins of Influenza and Vaccinia Viruses are Suppressors of RNA Silencing" *PNAS USA* 101(5):1350-1355 (2004).

Misquitta and Paterson. "Targeted Disruption of Gene Function in *Drosophila* by RNA Interference (RNA-i): A Role for *Nautilus* in Embryonic Somatic Muscle Formation" *PNAS USA* 96:1451-1456 (1999).

Silhavy et al. "A Viral Protein Suppresses RNA Silencing and Binds Silencing-Generated, 21- to 25-Nucleotide Double-Stranded RNAs" *The EMBO Journal* 21(12):3070-3080 (2002).

(56) References Cited

OTHER PUBLICATIONS

Silva et al. "RNA Interference: A Promising Approach to Antiviral Therapy?" *Trends Mol Med* 8(11):505-508 (2002).

Sledz et al. "Activation of the Interferon System by Short-Interfering RNAs" *Nat Cell Biol* 5(9):834-839 (2003).

Smith et al. "Immunostimulation in Crustaceans: Does it Really Protect Against Infection?" *Fish Shellfish Immunol* 15(1):71-90 (2003).

Svoboda et al. "Selective Reduction of Dormant Maternal mRNAs in Mouse Oocytes by RNA Interference" *Development* 127:4147-4156 (2000).

Vazquez et al. "Review: Immunity Mechanisms in Crustaceans" *Innate Immun* 15(3):179-188 (2009).

Wang and Barr. "RNA Interference in *Caenorhabditis elegans*" *Methods Enzymol* 392:36-55 (2005).

Wang et al. "RNA Interference Directs Innate Immunity Against Viruses in Adult *Drosophila*" *Science* 312(5772):452-454 (2006).

Japanese Office Action issued in Japanese Application No. 2006-518782 (19 pages) (English translation included).

Chinese Office Action issued in Chinese Application No. 200480025135.8 (11 pages) (English translation included).

English translation of Grounds of Rejection issued by the State Intellectual Property Office (SIP) for Chinese Application No. 200480025135.8 (11 pages) (Mar. 31, 2012).

English translation of Office Action for Japanese Application No. 2006-518782 (6 pages) (Feb. 2012).

Yang et al. "Complete Genome Sequence of the Shrimp White Spot Bacilliform Virus" *Journal of Virology* 75(23):11811-11820 (2001).

Warr & Browdy "Final Report: Double-Stranded RNA and the Anti-Viral Immune Response of Shrimp" (Dec. 30, 2004).

\* cited by examiner

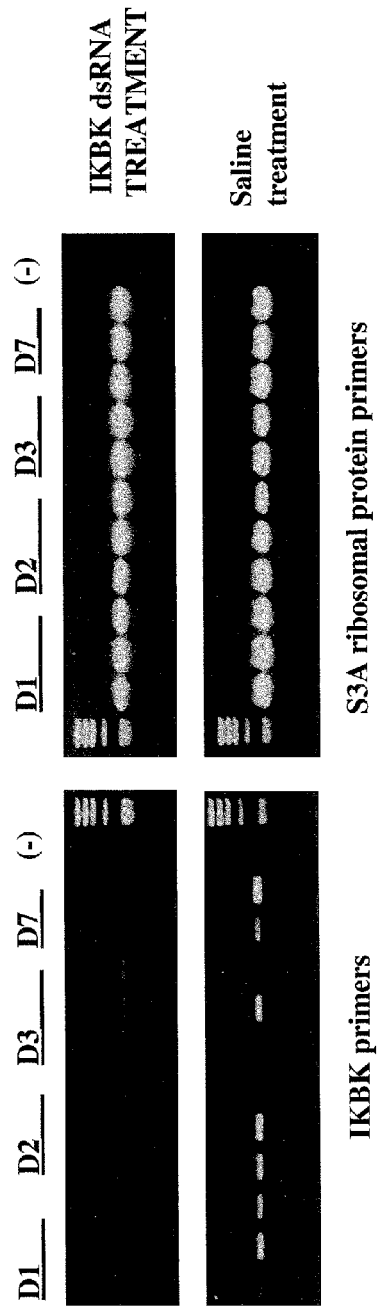
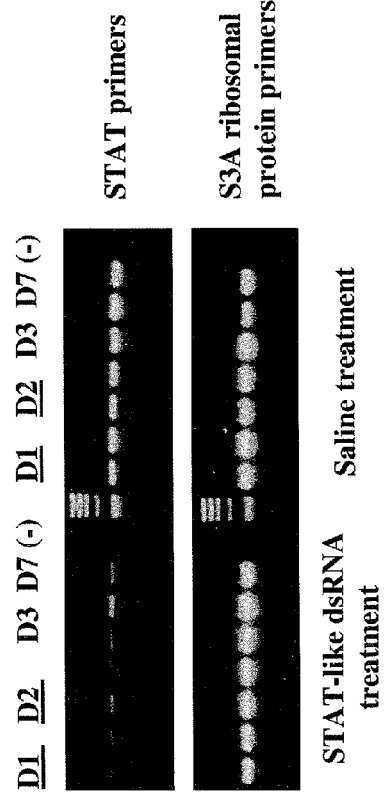
FIG. 1A
FIG. 1B

DSRNA INDUCED SPECIFIC AND NON-SPECIFIC IMMUNITY IN CRUSTACEANS AND OTHER INVERTEBRATES AND BIODELIVERY VEHICLES FOR USE THEREIN

This application claims priority to U.S. provisional application No. 60/564,295, filed Apr. 22, 2004, U.S. Ser. No. 60/484,531 filed Jul. 2, 2003, entitled "Methods and Compositions for Inducing Non-Specific Immune Responses in Crustaceans and Other Invertebrates", filed Sep. 25, 2003 (Ser. No. 60/505,715), and U.S. provisional No. 60/498,603 filed Aug. 29, 2003, all of which are incorporated by reference in their entireties herein.

This application also relates to grants awarded 1) by the USDA to the Oceanic Institute Administered US Marine Shrimp Farming Program and the South Carolina Department of Natural Resources Division for the FY03 Gulf Coast Shrimp Project, USDA/CSREES Award No. 2002-38808-01345 2) by the National Science Foundation to the Medical University of South Carolina, Award No. MCB 0315393 and 3) by the National Marine Fisheries Service to the South Carolina Department of Natural Resources, Award Nos. NA03NMF4720362 and NAO7FL0498.

FIELD OF THE INVENTION

The present invention provides a greater understanding of invertebrate immunity, preferably marine invertebrate immunity e.g., crustacean, and more particularly invertebrate antiviral immunity. The present invention further provides methods and materials for inducing a non-specific (systemic) immune response in an invertebrate, preferably a marine invertebrate, such as a crustacean (e.g., shrimp, lobster, crab), mollusk (e.g., snail, clam, squid, et al.) or other invertebrate by the administration of at least one double stranded RNA.

The present invention also provides methods and materials for inducing either or both a non-specific (systemic) immune response and a sequence specific RNA interference response in a crustacean or another invertebrate by the administration of at least one long or short double stranded RNA.

The present invention also provides methods and materials for enhancing RNA interference responses by the co-administration of at least one dsRNA that has a sequence that provides for targeted inhibition of a gene that contains a sequence that hybridizes thereto and a non-specific dsRNA which acts as an "adjuvant" in that its administration promotes (enhances) the immune response that is elicited by the administration of the first sequence-specific dsRNA. Said co-administration encompasses joint or separate administration of said sequence-specific dsRNA and non-specific dsRNA, effected in either order.

The present invention also specifically relates to the use of dsRNA to modulate expression of endogenous marine invertebrate genes, e.g., mollusk or crustacean genes, such as those involved in immunity, growth, reproduction, and general health or "robustness" as well as essential genes of pathogens that infect marine invertebrates, preferably mollusks and crustaceans. Such genes include, e.g., STAT, IKB and other putative components of the NFKB and STAT signaling pathways. Such genes also include those coding for neurotransmitters, hormones and metabolic pathways which include molt inhibiting hormone, gonad inhibiting hormone and crustacean hyperglycemic hormone. Such genes also include those coding for antimicrobial peptides or regulators for production of such peptides which include crustins and penaeidins. Potentially dsRNA can be used to down-regulate the expression of any desired marine-invertebrate, e.g., mollusk or crustacean gene. For example, putative target genes can be identified in genomic libraries, e.g., suppression subtractive hybridization libraries generated using control and viral (WSSV or TSV) infected shrimp tissues. Other specific examples of potential target genes include VP28, ribonucleotide reductase, hemocyanin, VP26, VP19, thymidylate kinase, and DNA polymerase.

Preferably, the invention involves the administration of a dsRNA having a sequence that is identical or which exhibits high sequence identity, e.g., at least 75%, more preferably at least 85-90%, and more preferably from 90-99% identical to a crustacean gene or a gene of a pathogen that normally infects a crustacean. In the case of shrimp, such pathogens include viruses such as White spot syndrome virus, Taura syndrome virus, Infectious hypodermal and hematopoietic necrosis virus (IHHNV), Baculovirus of penaeid shrimp (BP), Rhabdovirus of penaeid shrimp (RPS), Gill-associated virus (GAV), Yellow head virus (YHV), Lymphoid organ-associated virus (LOVV), Lymphoidal parvolike viral disease (LPV), Hepatopancreatic parvovirus (HPV), Baculoviral midgut gland necrosis virus (BMN), Monodon baculovirus (MBV) Reo like virus diseases (REO), Rhabdovirus (RPS) and emerging viruses for which essential genes may be identified and sequenced through any means available to those skilled in the art. (Emerging viruses refers to viruses as yet unidentified or later produced, e.g., by recombination or mutation, from known viruses. Emerging viruses may be isolated and identified, e.g., by comparison to known genomes of viruses and the genome of the wild-type shrimp e.g., by means of subtractive hybridization).

More specifically, the present invention provides methods and materials for inducing sequence-independent general antiviral protection in any invertebrate and specifically the marine crustacean, *Litopenaeus vannamei* and other shrimp, and potentially protection against other parasites e.g., bacteria, fungi, microsporidians, haplosporidians and gregarines.

Moreover, the present invention provides the first demonstration that an invertebrate immune system, analogous to its vertebrate counterparts, can recognize dsRNA as a virus-associated molecular pattern, resulting in the activation of an innate antiviral response.

Additionally, the present invention provides biodelivery vehicles for delivery of at least one dsRNA to a crustacean, mollusk or other invertebrate, preferably a shrimp, wherein the biodelivery vehicle is an organism such as a yeast or microalgae which stably or transiently expresses the dsRNA and which organism may be safely ingested by the crustacean or other invertebrate. In a preferred embodiment the invention provides recombinant yeast, e.g., *Saccharomyces*, or recombinant microalgae, e.g., *Chlamydomonas, Chlorella, Arthrospira* (*Spirulina*) et al., that express at least one heterologous dsRNA under the control of an inducible or constitutive promoter.

DESCRIPTION OF THE REALTED ART

The present invention relates to targeted and non-targeted methods of modulating, preferably inhibiting gene expression by the use of dsRNA molecules. Methods for achieving inhibition of gene expression are well known in the art. Such methods include the use of antisense nucleic acids, triple-helix approaches, co-suppression and RNA interference or RNA silencing.

Use of Antisense Nucleic Acids to Engineer Interference

Antisense technology has been the most commonly described approach in protocols to achieve gene-specific interference. For antisense strategies, stochiometric amounts of single-stranded nucleic acid complementary to the messenger RNA for the gene of interest are introduced into the cell. Some difficulties with antisense-based approaches relate to delivery, stability, and dose requirements. In general, cells do not have an uptake mechanism for single-stranded nucleic acids, hence uptake of unmodified single-stranded material is extremely inefficient. While waiting for uptake into cells, the single-stranded material is subject to degradation. Because antisense interference requires that the interfering material accumulate at a relatively high concentration (at or above the concentration of endogenous mRNA), the amount required to be delivered is a major constraint on efficacy. As a consequence, much of the effort in developing antisense technology has been focused on the production of modified nucleic acids that are both stable to nuclease digestion and able to diffuse readily into cells. The use of antisense interference for gene therapy or other whole-organism applications has been limited by the large amounts of oligonucleotide that need to be synthesized from non-natural analogs, the cost of such synthesis, and the difficulty even with high doses of maintaining a sufficiently concentrated and uniform pool of interfering material in each cell.

Triple-Helix Approaches to Engineer Interference

A second method for engineered interference is based on a triple helical nucleic acid structure. This approach relies on the rare ability of certain nucleic acid populations to adopt a triple-stranded structure. Under physiological conditions, nucleic acids are virtually all single- or double-stranded, and rarely if ever form triple-stranded structures. It has been known for some time, however, that certain simple purine- or pyrimidine-rich sequences could form a triple-stranded molecule in vitro under extreme conditions of pH (i.e., in a test tube). Such structures are generally very transient under physiological conditions, so that simple delivery of unmodified nucleic acids designed to produce triple-strand structures does not yield interference. As with antisense, development of triple-strand technology for use in vivo has focused on the development of modified nucleic acids that would be more stable and more readily absorbed by cells in vivo. An additional goal in developing this technology has been to produce modified nucleic acids for which the formation of triple-stranded material proceeds effectively at physiological pH.

Co-Suppression Phenomena and Their Use in Genetic Engineering

A third approach to gene-specific interference is a set of operational procedures grouped under the name "co-suppression". This approach was first described in plants and refers to the ability of transgenes to cause silencing of an unlinked but homologous gene. More recently, phenomena similar to co-suppression have been reported in two animals: *C. elegans* and *Drosophila*. Co-suppression was first observed by accident, with reports coming from groups using transgenes in attempts to achieve over-expression of a potentially useful locus. In some cases the over-expression was successful while, in many others, the result was opposite from that expected. In those cases, the transgenic plants actually showed less expression of the endogenous gene. Several mechanisms have so far been proposed for transgene-mediated co-suppression in plants; all of these mechanistic proposals remain hypothetical, and no definitive mechanistic description of the process has been presented. The models that have been proposed to explain co-suppression can be placed in two different categories. In one set of proposals, a direct physical interaction at the DNA- or chromatin-level between two different chromosomal sites has been hypothesized to occur; an as-yet-unidentified mechanism would then lead to de novo methylation and subsequent suppression of gene expression.

RNA Interference or RNA Silencing

A further process for inhibiting expression of a target gene in a cell or animal is RNA interference (RNAi) or RNA silencing. The process comprises the introduction of RNA with partial or fully double-stranded character (dsRNA) into a cell or into the extracellular environment thereof. Inhibition is specific in that a nucleotide sequence from a portion of the target gene is chosen to produce the double stranded inhibitory RNA. This process is (1) effective in producing inhibition of gene expression, (2) specific to a targeted gene, and (3) allows for the inhibition of the expression of many different types of target genes.

For example, the target gene may be a gene derived from the cell, an endogenous gene, a transgene, or a gene of a pathogen which is present in the cell after infection thereof. Depending on the particular target gene and the dose of double stranded RNA material delivered, the procedure may provide partial or complete loss of function for the target gene.

Methods and materials for use in inhibiting the expression of target genes by RNA interference or RNA silencing have been reported in several issued patents and many recently published patent applications. See, e.g., U.S. Pat. No. 6,506,559 by Fire et al.; U.S. Pat. No. 6,326,193 by Liu et al.; WO 99/49029 by Graham et al.; and U.S. Pat. No. 6,573,099 by Graham et al.

With respect to the foregoing, the RNA interference methods and materials patented by Graham (assigned to Benitec) require the use of an isolated DNA construct comprising at least two copies of a sequence corresponding to a target gene, the expression of which is to be delayed, repressed or inhibited, both of which are operably linked to a single promoter, in the sense orientation. By contrast, the RNA interference methods recited in the Fire patents recite use of any double stranded molecule, wherein the first strand consists essentially of a ribonucleotide sequence that corresponds to a nucleotide sequence of a target gene, and the second strand is complementary to the nucleotide sequence of the target gene, such that these two strands hybridize to form a double stranded RNA molecule that inhibits the expression of a target gene.

RNA interference is mechanistically a two-step process. In the first step, dsRNA triggers a silencing response that results in cleavage of dsRNA into small interfering RNAs of 21-23 nucleotides. The cleavage is accomplished by Dicer, an RNase-III family nuclease. In the second step, siRNAs are incorporated into a targeting complex, RISC, (RNA-induced silencing complex) which destroys mRNAs that are homologous to the integral siRNA (Silver et al., Trends in Mol. Med. 8(11):505-508 (2002)).

RNA interference has recently been reported to be a powerful tool for probing gene function and to have potential for developing novel antiviral therapeutics. (Silver et al.. (Id.)). However, while the RNAi pathway has been recognized as a conserved biological process, it is one that is not yet fully understood and which exerts variable effects in different species. For example, while dsRNA can induce the degradation of homologous RNAs in organisms including some protozoans, animals, plants and fungi, resulting in pos-transcriptional gene silencing; in some species; RNA-mediated processes can alternatively result in translational repression, DNA methylation, heterochromatin formation and DNA elimination. In some situations, amplification of the 'trigger' double-stranded RNA is required for efficient silencing (Cerutti et al., Trends in Genetics 19(1):39-46 (2003)).

Most RNAi research to date has focused on the sequence-specific effects of dsRNAs on the levels of expression of target genes. However, it is also known that the administration of dsRNA elicits a systemic (non-sequence specific) immune response in vertebrates. For example, Sledz et al., Nature Biol. Advance Online Publication report the activation of the interferon system in a mammalian system by the administration of short-interfering RNAs. Specifically, Sledz et al (Id.) produced 21 nucleotide long dsRNAs, specific to the lamin and GAPDH genes and reported that they induced interferon-mediated activation of the JAK-Stat pathway and global upregulation of IFN-stimulated genes. (Id.) This systemic response effect reportedly was mediated by the dsRNA-dependent protein Kinase (PKR), which is activated by siRNA and is required for up-regulation of IFN-β in response to siRNAs.

Although the invertebrate immune system has been well studied in the context of antibacterial and antifungal responses, there is no information at the cellular or molecular level regarding an invertebrate immune response directed against viruses. By contrast, in mammals, antiviral and antibacterial innate responses include partially overlapping, but distinct pathways, with the interferon system comprising the most prominent innate antiviral response.

Interferons (IFN) are well known to comprise a family of cytokines which are expressed in response to viral infection and other insults, and regulate a myriad of cellular and systematic responses directed to control viral propagation (see Levy et al., Cytokine Growth Factor Rev. 12:143-156 (2001) and Goodburn et al., J. Gen. Virol. 81:2341-2364 (2000) for a review). Upon induction of cells by circulating IFN, signal transduction through the Janus kinase/Signal Transducer and Activator of Transcription (JAK/STAT) system results in the induction of hundreds of genes (de Veer et al., L. Leuc. Proc. Biol. 69:;912-20 (2001); Ehrt et al., J. Exp. Med. 194:1123-40 (2001)). IFN inducible genes include those encoding RNA-dependent protein kinase (PKR), the Mx protein, oligoadenylate synthetase (OAS), and IFNs themselves. This self-amplifying system can be triggered not only by IFN, but also directly by viral components. A potent inducer of the IFN response is double stranded RNA (dsRNA), a molecule that often occurs during viral infection as a result of viral genomic replication and viral RNAs with extensive secondary structure (review in (Jacobs et al., Virology 219:339-49 (1996))). In mammals dsRNA is recognized by the TLR3 receptor, which activates myeloid differentiation factor 88 (Myd88)-dependent and independent signal transduction cascades, leading to the expression of IFNβ. dsRNA also induces antiviral responses intracellularly, by directly activating PKR, which leads to inhibition of cellular and viral protein synthesis via phosphorylation of eukaryotic translation initiation factor 2a (eIF2a) (Meurs et al., Cell 62:379-90 (1999)). It has been generally accepted that these dsRNA-induced immune responses are absent from invertebrates, a conclusion supported by the lack of genes having a structure homologous to IFNs or to the major effectors of the IFN response (e.g. PKR, Mx, OAS) in several fully-sequenced invertebrate genomes (Adams et al., Science 287: 2187-95 (2000); The C. elegans Sequencing Consortium Science 282:2012-80 (1998); Dehol et al., Science 298:2157-2167 (2002); Hot et al., Science 298:129-49 (2002)).

Recently, the complexity of the biological properties of dsRNA in vivo has become more understood with the discovery of dsRNA-mediated post-transcriptional gene silencing (PTGS or RNAI). This phenomenon is observed in both plants and animals, vertebrates and some invertebrates such as nematodes (Fire et al., Nature 391:806-11 (1998)), and insects (Misquitta et al., Proc. Natl. Acad. Sci. USA 9-0: 451-6 (1999)), and mammals (Svoboda et al., Devel. 127: 4147-56 (2000)). This process comprises dsRNA being processed into short duplexes 21-25 bp long, known as short interfering RNAs (siRNAs) by the RNase III Dicer (Burnstein et al., Nature 409:363-6 (2001)). These siRNAs are utilized to recognize homologous mRNAs and trigger their degradation by RNase activities associated with the RNA-induced silencer complex (RISC) (Hammond et al., Nature 404:293-6 (2000); Hammond et al., Science 293:1146-50 (2001)). It has been proposed that RNAi represents an ancient antiviral mechanism used to inhibit the expression of viral gene products in infected cells, because viral dsRNAs often occur in the course of infection. For instance, viral strategies to evade the RNAi pathway exist in both plant and animal viruses (Li et al., Science 296:1319-21 (2002); Li et al., Proc. Natl. Acad. Sci., USA 101:1350-5 (2004); and Silhavy et al., EMBO J., 21:3070-80 (2002)).

Whereas the sequence-specific effects of dsRNA that result in engodenous RNA degradation are widely conserved, and probably present in most invertebrates, the sequence-independent induction of antiviral immunity by dsRNA has long been thought to be exclusive to vertebrates.

Quite unexpectedly, the present inventors discovered that the administration of a non-specific dsRNA (dsRNA which does not exhibit homology to any known endogenous invertebrate gene) elicits a generic, anti-viral response at least in the marine shrimp *Litopenaeus vannamei*, and based on these results, probably other crustaceans and invertebrates. This invention provides the first evidence that invertebrates are capable of displaying inducible antiviral immunity in response to a bona fide virus-associated molecular structure (dsRNA). The inventive discovery suggests that innate antiviral immunity in invertebrates shares some of the molecular features of vertebrate antiviral responses, including an immune response that is inducible by dsRNA.

Recently, Timmons et al., (Mol. Biol. Of the Cell 13:2972-2983 (July 2003)) reported in an invertebrate system that dsRNA can elicit a gene-specific RNA interference response which also has a systemic character, i.e., silencing of gene expression is observed in cells distal from the site of dsRNA delivery. In a *C. elegans* system, Timmons et al. (Id) reported that transgenic strains of *C. elegans*, transcribing dsRNA from a tissue-specific promoter do not exhibit comprehensive systemic RNA interference phenotypes. They further reported that exogenous delivery of unrelated dsRNA molecules elicited a detectable systemic RNA silencing phenotype, but that animals defective in fed-1 or fed-2 were unable to mount a robust systemic silencing response to ingested dsRNAs. Timmons et al (Id.) suggest that this raises the possibility of multiple and/or tissue specific mechanisms for cellular uptake and export of RNA silencing signals.

Prior to the invention, little had been known about crustaceans' immune mechanisms. Particularly, it was known that crustaceans possess some rudimentary humoral and cellular defense mechanisms. Humoral immune reactions include blood clotting, the activation of the prophenoloxidase cascade, and the production and release of antimicrobial peptides that are active against some bacteria and fungi. Cellular defense mechanisms involve primarily circulating hemocytes which are involved in encapsulation, phagocytosis and intracellular killing of pathogens. Crustacean phagocytic hemocytes show a typical respiratory burst that results in the production of reactive oxygen species. It was also known that cells synthesize some effective antimicrobial molecules. Particularly, the gills of the blue crab (*Callinectes sapidus*) and the marine shrimp (*Penaeus monodon*) also clear some foreign proteins from the blood via an unexplained molecular pathway. Also, recently, putative components of the Toll/NFKB pathway were reported to be present in oyster, and the horseshoe crab. However, the function of these genes, if any, remains unknown, and can not be predicted absent proof, especially in view of the divergency of function of Toll/NFKB genes in different species.

However, nothing suggested that crustaceans or other invertebrates were capable of producing a non-sequence specific immune response to dsRNAs. Indeed, a recent review article by Lee and Soderhall (Fish & Shellfish Immunol. 14:421-437 (2002)), which provides a detailed overview of what is presently understood about crustacean innate immunity, does not include any suggestion that dsRNAs are involved. (Id.) Moreover, a recent article by Smith et al., Fish & Shellfish Immunol. 10:1-20 (2003), questioned the very efficacy of the role of immunostimulation in crustaceans as a means of protecting against viral infection and noted the potential risks to the wellbeing of stock animals by the use of putative immunostimulants. This article, similarly, while referencing key proteins believed to be involved in crustacean immunity, contains no suggestion that crustaceans are capable of responding to dsRNAs.

Indeed, the systemic effects of dsRNA in crustaceans and other invertebrate species, were unknown prior to the invention. Moreover, it was unknown prior to the invention that crustaceans, particularly shrimp, and most probably other marine invertebrates possess the requisite cellular machinery to elicit an RNA interference response.

OBJECTS OF THE INVENTION

Thus, it is an object of the invention to provide a greater understanding of invertebrate immunity, e.g., crustacean immunity. (While the invention in its experimental section exemplifies that subject discovery in crustaceans, particularly shrimp, it is anticipated that the subject methods will be useful in other invertebrates, and most especially invertebrates that are closely related to crustaceans e.g., other marine invertebrates such as shelled and unshelled mollusks, e.g., squid, clams, octopus, slugs, snails, et al.; *Porifera* (sponges); *Cnidaria* (jellyfish, coral, hydroids), *Ctenophora* (comb jellies), *Echinodermata* (Sea Stars, Brittle Stars) and marine worms. However, the invention embraces other invertebrates which include by way of example insects, arachnids, centipedes and millipedes).

It is another object of the invention to provide novel methods for inhibiting gene expression and/or inducing systemic immune responses in invertebrates, particularly systemic antiviral immunity, or immunity against other parasites that infect invertebrates, e.g., bacteria or fungi by the administration of at least one double stranded RNA.

It is a more specific object of the invention to provide methods of inducing a non-specific (systemic) protective immune response in an invertebrate, preferably a marine invertebrate such as a crustacean, and more preferably a shrimp, by the administration of at least one double stranded RNA that induces a protective, non-specific (systemic) immune response against different pathogens, that infect such invertebrate, e.g., viruses, bacterium, fungi, nematode, mycoplasma, microsporidians, haplosporidians, gregarines and most preferably viruses, e.g., crustacean associated viruses.

It is also an object of the invention to provide methods of inducing in a crustacean, preferably a shrimp, a sequence-specific dsRNA-mediated response that inhibits the expression of a targeted gene endogenous to said crustacean, or an essential gene comprised in a pathogen that infects said crustacean, by the administration of at least one long double stranded RNA, which possesses a sequence substantially corresponding to a target gene comprised in said crustacean or pathogen, e.g., a virus, wherein said sequence-specific immune response effects sequence-specific protection against a parasite, e.g., a virus.

It is further an object of the invention to induce in a crustacean, e.g., a shrimp both a non-specific (systemic) immune response and a sequence-specific RNA interference response that inhibits or prevents expression of a target gene, wherein said target gene is a crustacean gene or an essential pathogen gene, and wherein the combination of said systemic immune response and said sequence-specific dsRNA response confers protection against a pathogen that normally infects said crustacean, e.g., a virus, bacterium, fungi, nematode, mycoplasma, haplosporidian, microsporidian or gregarine by the administration of at least one double stranded RNA, wherein at least one of said administered dsRNAs has a sequence substantially corresponding to, or identical to a sequence comprised in a target gene contained in the crustacean or pathogen that infects said crustacean. For example, putative target genes can be identified in genomic libraries, e.g., suppression subtractive hybridization libraries generated using control and viral (WSSV or TSV) infected shrimp tissues. Other specific examples of potential target genes include VP28, ribonucleotide reductase, hemocyanin, VP26, VP19, thymidylate kinase, and DNA polymerase.

Specific examples thereof include dsRNAs corresponding to crustacean genes involved in immunity, growth, reproduction, and general health or "robustness" and essential genes of pathogens. Such genes include e.g., STAT, IKB and other putative components of the NFKB and STAT signaling pathways. Such genes also include those coding for neurotransmitters, hormones and metabolic pathways which include molt inhibiting hormone, gonad inhibiting hormone, crustacean hyperglycemic hormone. Such genes also include those coding for antimicrobial peptides or regulators for production of such peptides which include crustins and penaeidins. Potentially dsRNA can be used to down-regulate the expression of any desired crustacean gene.

It is another preferred object to enhance the efficacy of RNA interference by co-administering a non-specific dsRNA (e.g., poly C:G) and a sequence-specific dsRNA (that targets a specific gene), whereby said non-specific dsRNA acts as an "adjuvant" and enhances the effect of said sequence-specific dsRNA on the expression of a target gene.

In preferred embodiments, dsRNA will be administered to a crustacean or other marine invertebrate, preferably a shrimp and the pathogen will be a shrimp virus, e.g., White Spot Syndrome Virus (WSSV) Taura Syndrome Virus (TSV), Infectious hypodermal and hematopoietic necrosis virus (IHHNV), Baculovirus of penaeid shrimp (BP), Rhabdovirus of penaeid shrimp (RPS), Gill-associated virus (GAV), Yellow head virus (YHV), Lymphoid organ-associated virus (LOVV), Lymphoidal parvolike viral disease (LPV), Hepatopancreatic parvovirus (HPV), Baculoviral midgut gland necrosis virus (BMN), Monodon baculovirus (MBV) Reo like virus diseases (REO), Rhabdovirus (RPS) and emerging viruses for which essential genes may be sequenced through any means available to those skilled in the art. (As noted previously, viruses refers to viruses as yet unidentified or later produced, e.g., by recombination or mutation, which may be isolated or identified, e.g., by comparison to the wild-type shrimp genome (e.g., by means of subtractive hybridization).

It is also an object of the invention to use functional genomics to identify putative orthologs of genes involved in invertebrate immunity particularly marine invertebrate immunity, and preferably crustacean (e.g., shrimp) immune responses, growth, reproduction, and general health or robustness particularly shrimp immune responses, e.g., STAT-like and I-KB Kinase-like genes.

It is a specific object of the invention to produce invertebrate cells or animals, preferably crustacean cells or animals having impaired or deleted expression of a putative immune regulatory gene in order to confirm gene function and its role in affording protection against viruses and/or other endogenous parasites.

It is another object of the invention to identify compounds that up-regulate or down-regulate genes that are involved in marine invertebrate, e.g., crustacean immunity, growth, reproduction, and general health or "robustness", e.g., STAT-like and I-KB Kinase-like genes, and ascertain the role of these genes in crustacean antiviral immunity and inflammation.

It is yet another object of the invention to identify specific invertebrate genes, preferably marine invertebrate, e.g., crustacean genes and more preferably shrimp genes which are up-regulated or down-regulated after the induction of a non-specific (systemic) immune response, elicited by the administration of at least one double-stranded RNA or viral infection. Functional analysis of these genes, e.g., STAT-like, Toll, NFKB, and "cytokine-like" genes, will facilitate a greater understanding of innate invertebrate immunity, particularly crustacean immunity, and further will allow for the identification of compounds that modulate the expression of such genes which therefore can be used to modulate innate invertebrate immune responses.

It is another object of the invention to produce biodelivery vehicles, preferably microbial biodelivery vehicles such as microalgae and yeast which express heterologous dsRNAs, e.g., dsRNAs that are specific to an essential gene of a pathogen that infects a crustacean e.g., a crustacean associated virus, bacterium, microsporidian, haplosporidian or gregarine, or an endogenous crustacean gene, e.g., a gene involved in immunity, growth, reproduction, and general health or "robustness" and/or which express at least one long dsRNA that elicits a generic immune response.

It is a specific object of the invention to provide a yeast (preferably *Saccharomyces*) or a microalgae that expresses at least one dsRNA e.g., dsRNA that is specific to an essential gene of a pathogen that infects a crustacean e.g., a crustacean associated virus, bacterium, microsporidian, haplosporidian or gregarine,, or an endogenous crustacean gene, e.g., a gene involved in immunity, growth, reproduction, and general health or "robustness" and/or which express at least one long dsRNA that elicits a generic immune response, wherein expression is preferably under the regulation of an inducible promoter.

It is another object of the invention to deliver a desired dsRNA to a marine invertebrate, e.g., crustacean or mollusk, preferably a shrimp, by contacting said crustacean, e.g., a shrimp with a culture medium containing said dsRNA, or a food that comprises at least one microorganism, preferably a yeast or a microalgae that expresses said dsRNA, e.g., e.g., dsRNA that is specific to an essential gene of a pathogen that infects a crustacean e.g., a crustacean associated virus, bacterium, microsporidian, haplosporidian or gregarine,, or an endogenous crustacean gene, e.g., a gene involved in immunity, growth, reproduction, and general health or "robustness" and/or which express at least one long dsRNA that elicits a generic immune response, wherein expression is preferably under the regulation of an inducible promoter.

DETAILED DESCRIPTION OF THE FIGURES

FIGS. 1A-B: dsRNA mediates systemic and sequence-specific mRNA depletion in *L. vannamei*: Shrimp (1-2 g) were injected intramuscularly with 10 μg of dsRNA or saline. FIG. 1A: Shrimp (1-2 g) were injected with 10 μg of dsRNA spanning 376 bp of the IKBK EST clone or with saline, and then sampled at different time points for extraction of gill total RNA. The 335 bp region of the transcript amplified during RT-PCR does not overlap the region utilized to synthesize the dsRNA. HaeIII-digested φx174 DNA was used as standard. Negative controls (−) were cDNA mock samples where either no RNA template or no reverse transcriptase was included. The time in days (D1 through D7) post injection at which animals were sampled, as well as the primers used in each panel are indicated. FIG. 1B: Shrimp (1-2 g) were injected with 10 μg of dsRNA spanning 370 bp of the STAT EST clone or with saline, and then sampled at different time points for extraction of gill total RNA. The 314 bp region of the transcript amplified during RT-PCR does not overlap the region utilized to synthesize the dsRNA. Controls and labels are as for FIG. 1A.

Figure 2B:
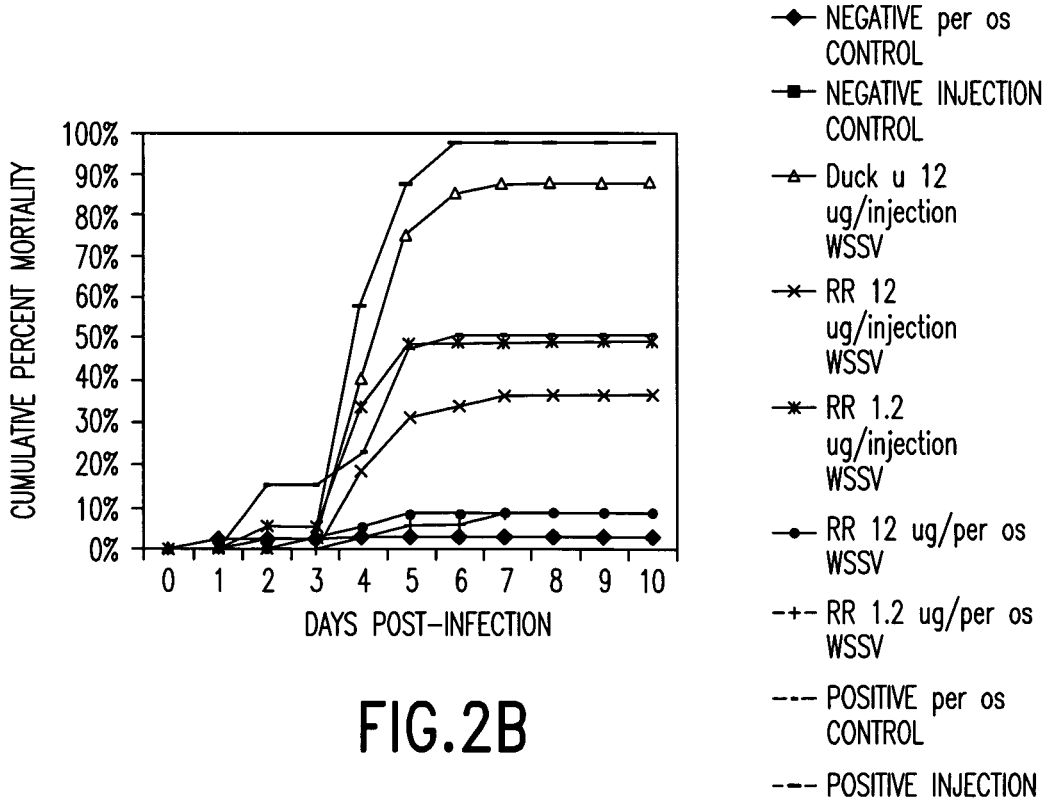

FIG. 2. dsRNA for WSSV genes protects against WSSV infection of *L. vannamei*: Shrimp (1-2 g) were injected intramuscularly with either saline or specific dsRNA together with a tissue extract containing WSSV at a 1:3 million w/v dilution. Negative controls were injected with specific-pathogen-free shrimp (SPF) extracts at similar w/v dilutions. For per os infections, animals were injected dsRNA and then fed 0.01 g of WSSV-infected muscle tissue or SPF tissue for 2 hours. In panel a, duck υ, ribonucleotide reductase (RR), DNA polymerase (DP), or vp28 (28) dsRNAs were used at 12 μg per animal. In panel b, duck υ dsRNA was also used at 12 μg per animal, while RR dsRNA was-used at 12 or 1.2 μg per animal, as indicated.

Figure 3:
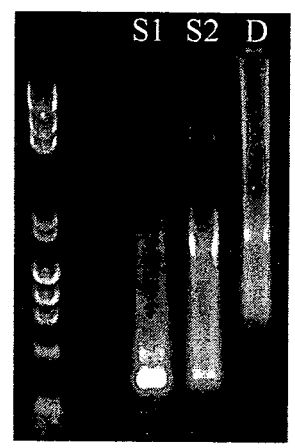

FIG. 3 contains an agarose gel electrophoresis experiment of single and double-stranded vp19 RNA. The two single-stranded (S1 and S2) synthesized by in vitro transcription were annealed to form dsRNA (D). Approximately 2 μg were loaded in each lane.

Figure 4A:
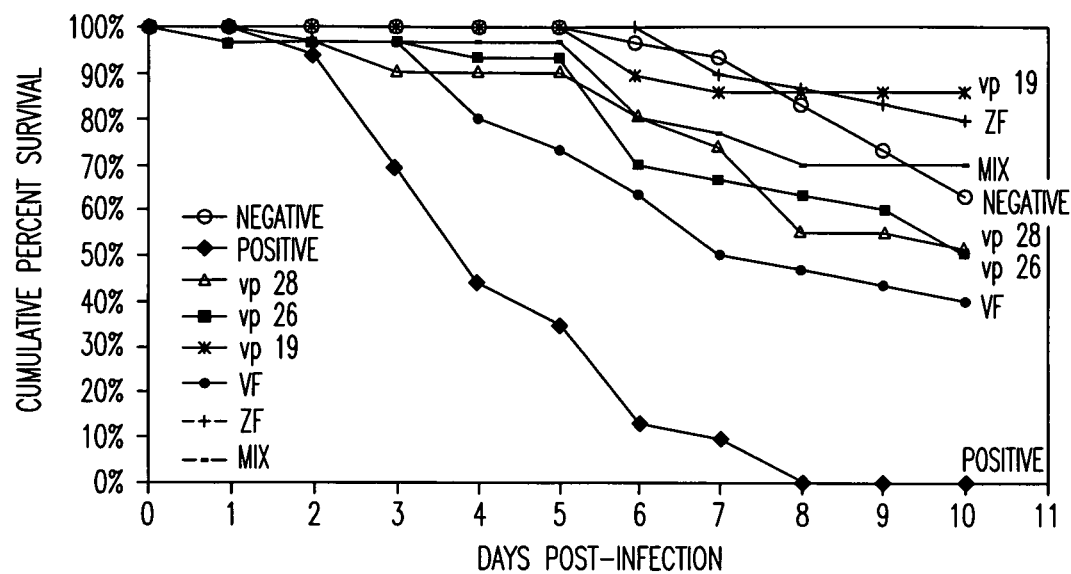
Figure 4B:
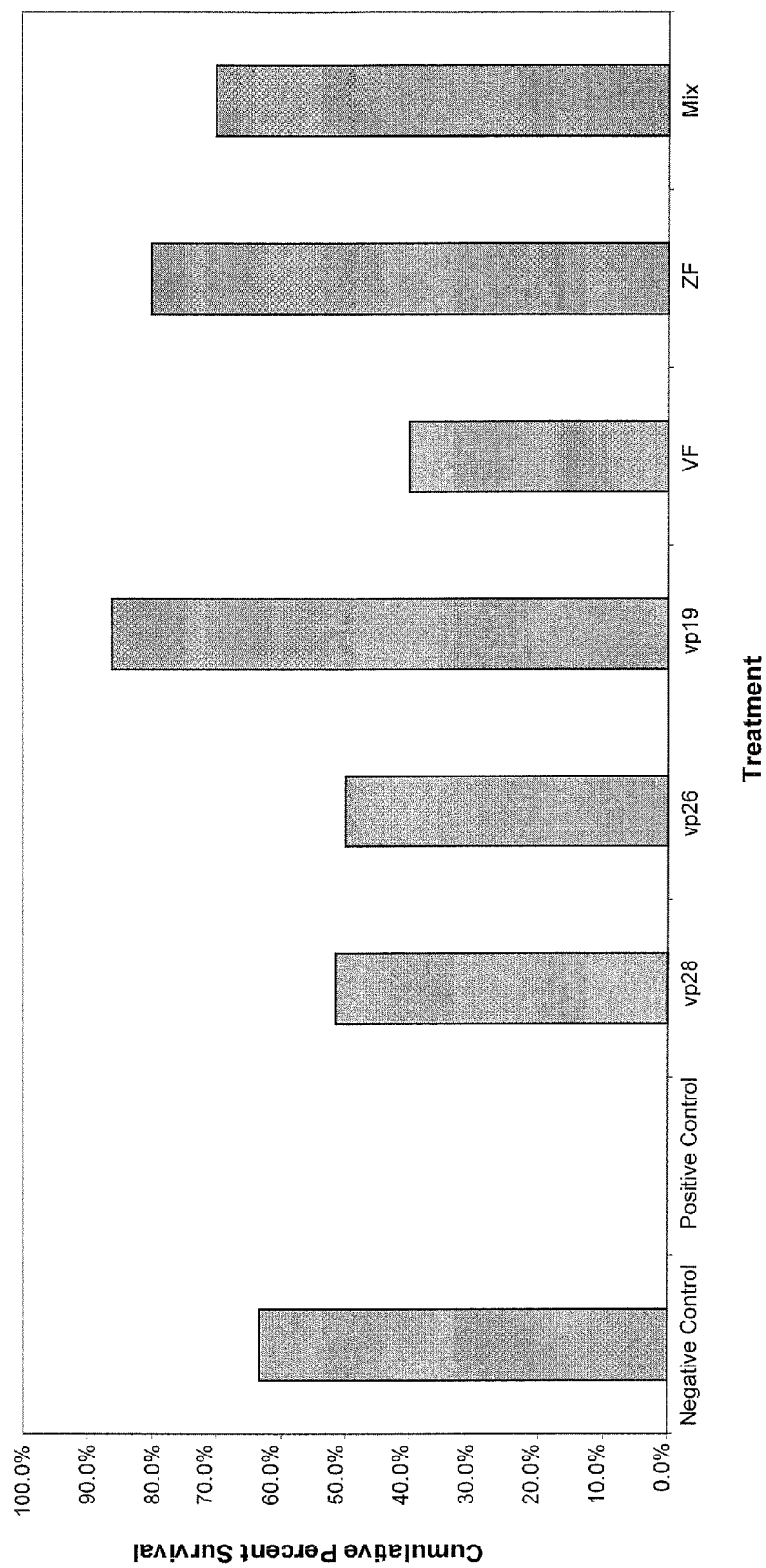

FIG. 4 compares the effects of dsRNA encoding 5 genes of WSSV, or a mixture of ten, on survival following challenge with the WSSV virus.

Figure 5A:
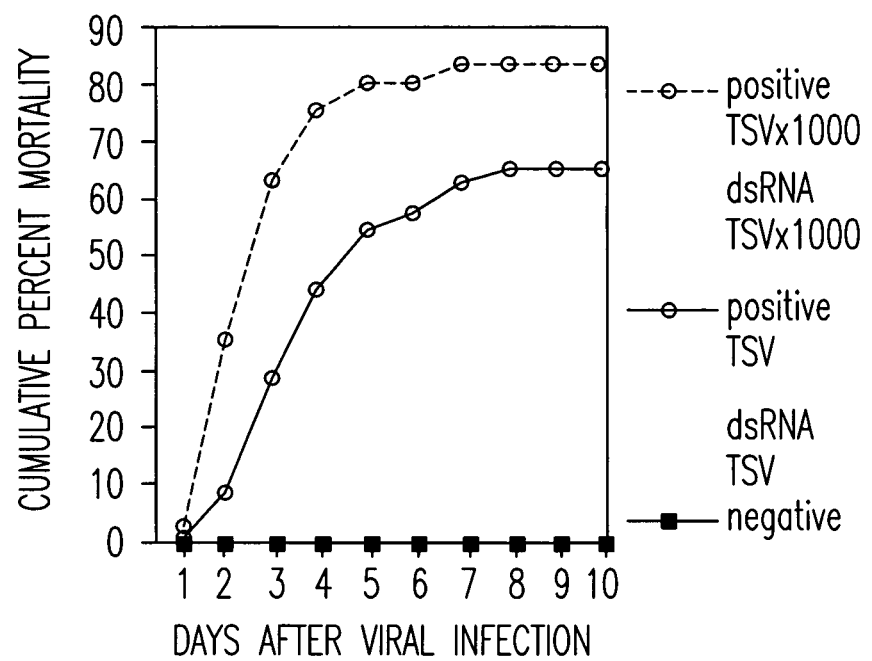
Figure 5B:
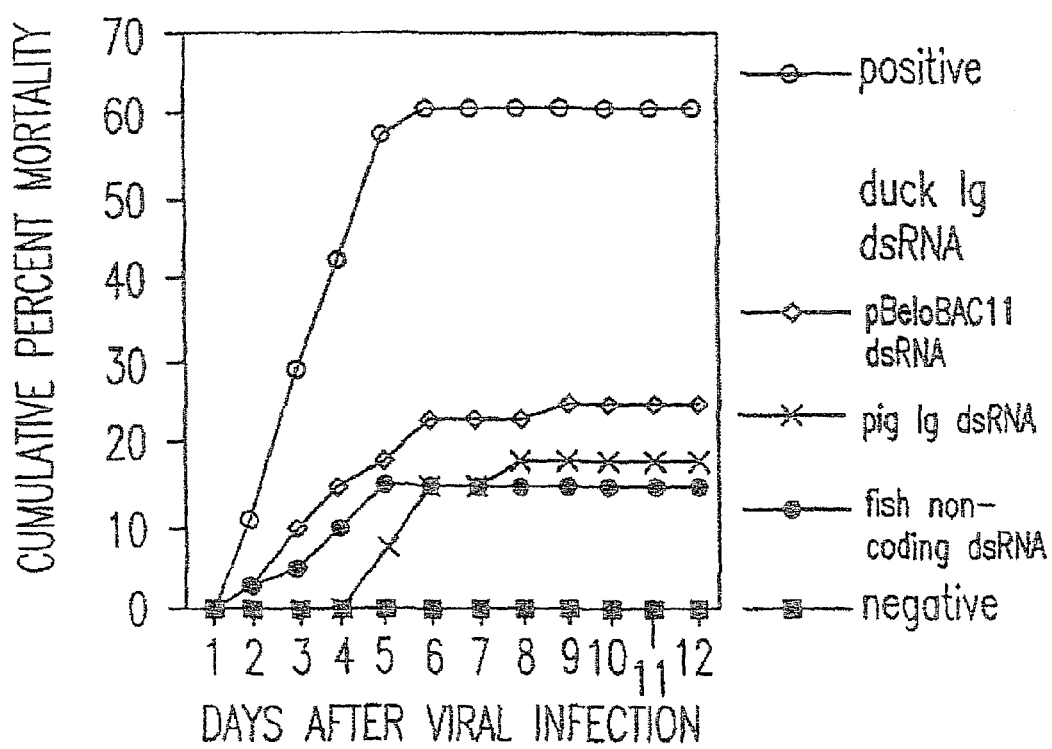
Figure 5C:
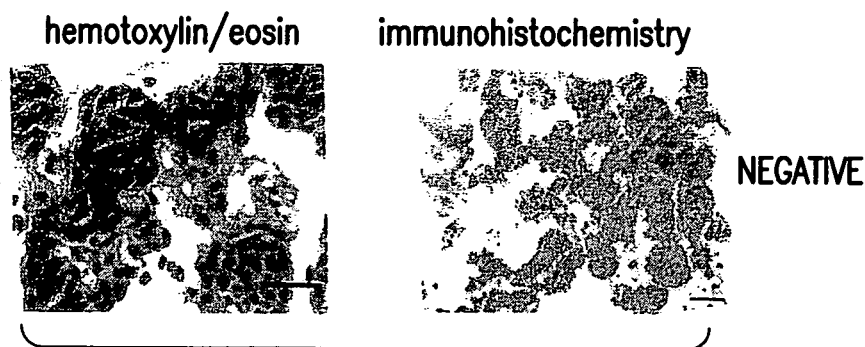
Figure 5D:
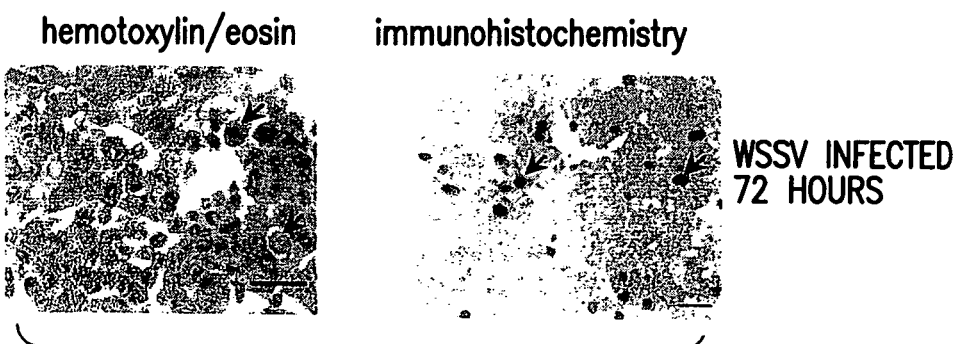
Figure 5E:
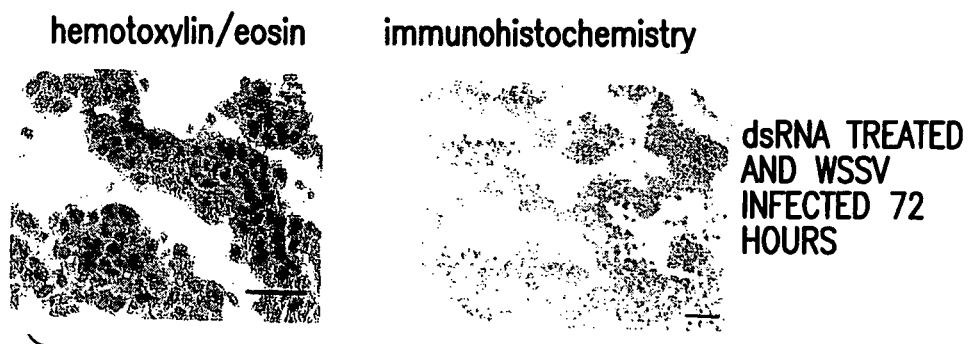

FIGS. 5A-E. dsRNA induces an antiviral state in shrimp. FIG. 5A: Shrimp (1-2 g) were injected intramuscularly with saline (positive and negative controls) or with 8 micrograms of dsRNA representing a portion of the cDNA for a duck Igυ(NCBI accession #AJ312200). 72 hours after dsRNA injection, animals were infected by intramuscular injection with TSV. The effect of a 1000-fold increase in the dose of TSV (from 1:100 million to 1:100,000 w/v dilutions) in positive controls and in dsRNA-treated shrimp is shown. FIG. 5B: Shrimp (1-2 g) were injected intramuscularly with saline (positive and negative controls) or with 8 micrograms of the indicated dsRNA. 72 hours after dsRNA injection, animals were infected by intramuscular injection with WSSV. The dsRNA preparations used to pre-treat shrimp were: a 309 bp portion of a gene encoding a duck Igυ(NCBI accession #AJ312200); a 1316 bp genomic non-coding region of clone BAC6 from the catfish IgH locus (NCBI accession #CC936713); a 1079 bp portion of pig IgG cDNA (NCBI accession #U03778); and a 1184 bp fragment of the bacterial artificial chromosome (BAC) cloning vector pBeloBAC11 (Kim et al., Genomics 34:213-8 1996)). In both FIGS. 5A-B, the number of shrimp in each experimental group was between 38 and 42. FIGS. 5C, D and E show eosin/hematoxylin staining and anti-WSSV immunostaining of hemopoietic tissue sections from an infected shrimp (FIG. 5D), in comparison with a non-infected shrimp (FIG. 5C) and a dsRNA-treated/WSSV-infected shrimp (FIG. 5E). The sections shown were obtained 72 hours after viral infection. Scale bars represent 20 microns.

Figure 6A:
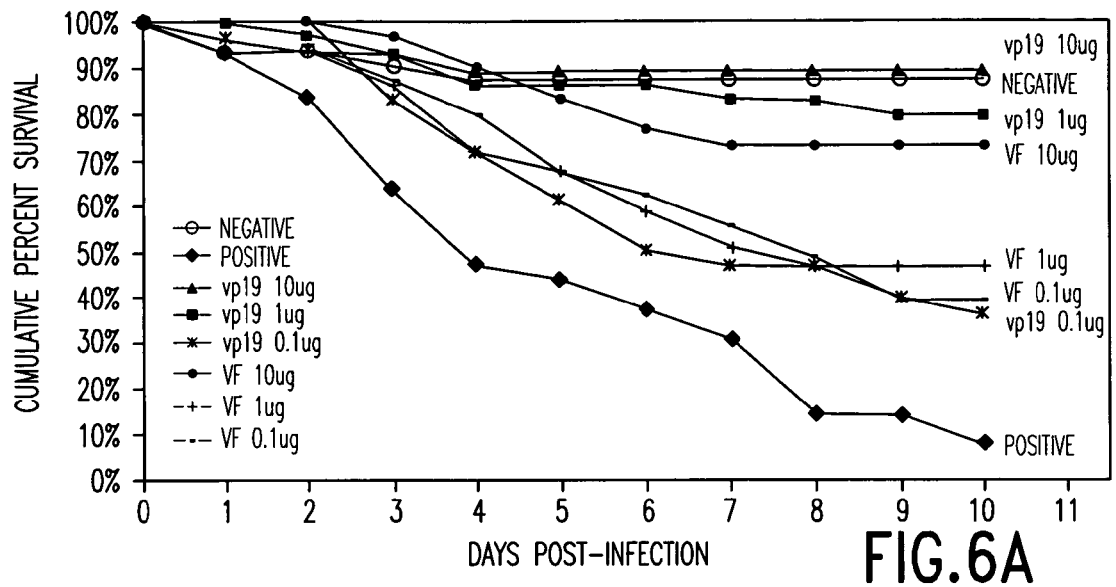
Figure 6B:
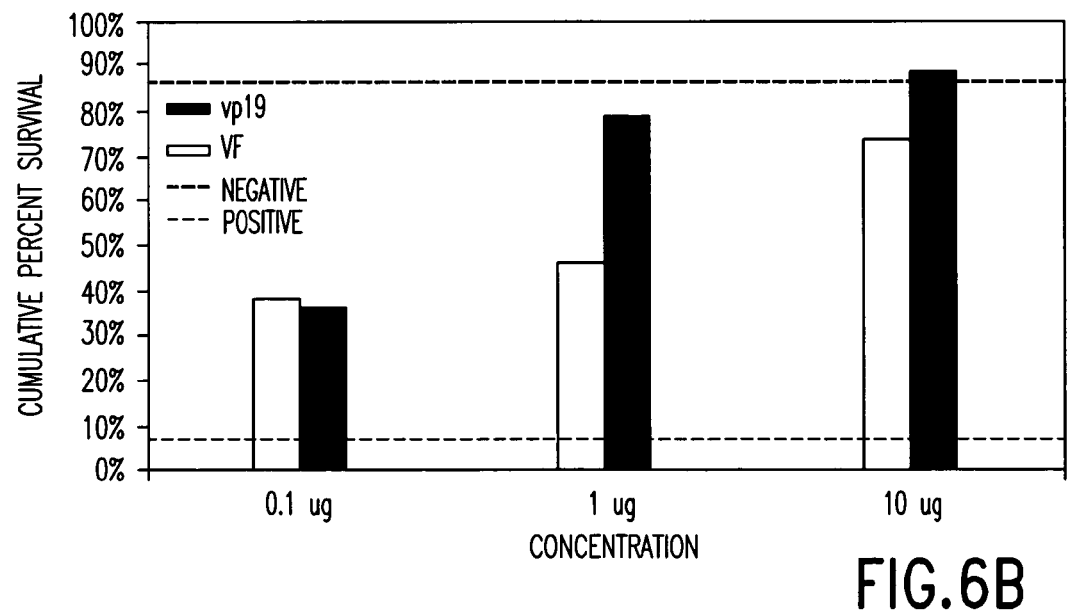

FIG. 6. contains an experiment which shows the protective effect of dsRNA against WSSV infection can be titrated out with dose.

Figure 7A:
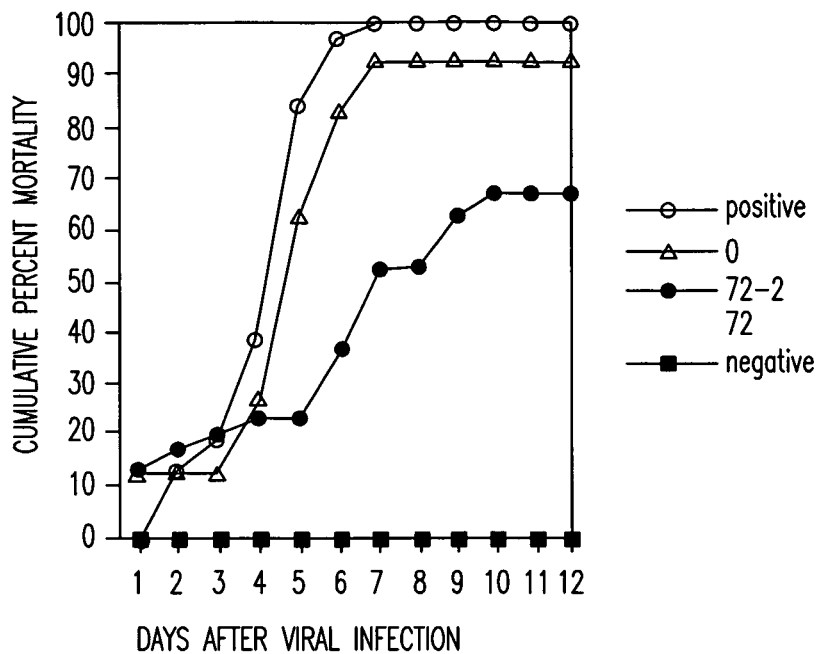

FIG. 7. Induction of the antiviral state is due to RNA: Shrimp (2-3 g) were injected intramuscularly with either saline (positive (–⊖–) and negative (–■–) controls) or dsRNA. 72 hours after this initial injection, animals were infected with WSSV either alone or mixed with dsRNA. a) animals (n=26-31) were injected each with 50 μl of a solution containing approximately 10-15 μg of dsRNA for the duck υ. and challenged with WSSV-positive extract. The 72-0 group (–●–) received dsRNA both 72 hours and 0 hours (co-injection) before viral infection, the 72 group (–▲–) received dsRNA only 72 hours prior to infection, and the 0 group (–⊖–) received dsRNA only mixed with WSSV inoculum. b) Shrimp (n=20=28) were kept in a recirculation system (see Materials and Methods), injected with dsRNA 72 hours before viral challenge, and then re-injected with dsRNA mixed with WSSV-positive extract. Positive (–⊖–) and negative (–■–) controls were as described for panel a. dsRNA for the duck υ. was used in every case, and applied at 10-15 μg per injection. dsRNA was purified with phenol and chloroform ((–△–)), RNeasy columns (Qiagen) (–●–), or purified with RNeasy columns and treated with a cocktail of RNases (RNase A, RNase T1, and RNase V1 from Ambion) (–⊟–). Fisher's exact test was used to assess the significance of the observed antiviral protection, by comparing the final cumulative mortality in dsRNA-treated groups with that in positive controls: a) 72-0 treatment (p–0.0003); 72 treatment (p=0.0001); panel b) dsRNA column (p=0.0017); dsRNA solvent (p=0.0003).

Figure 8A:
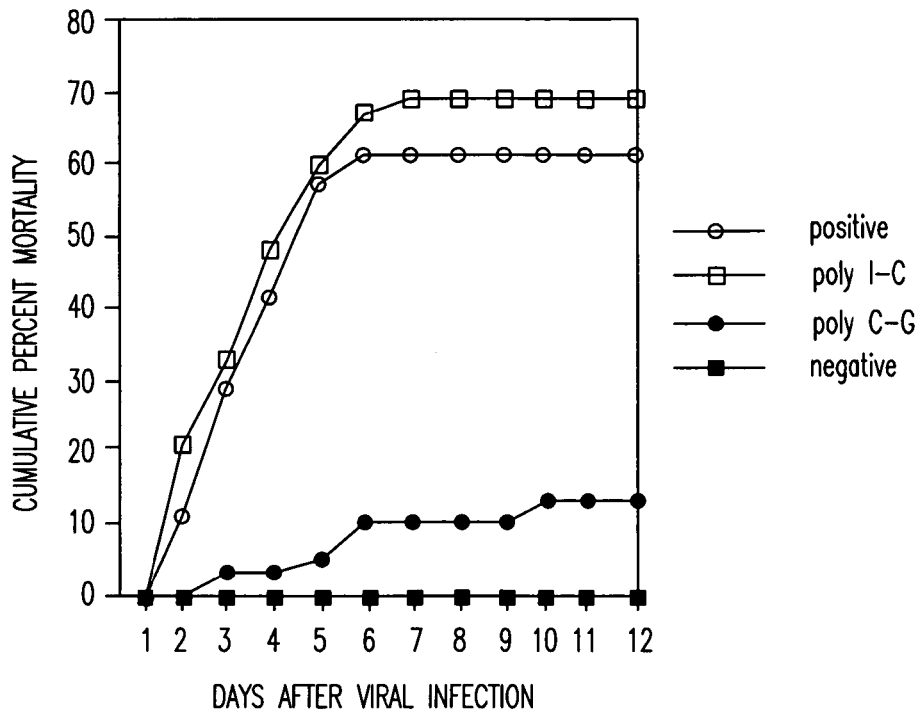
Figure 8B:
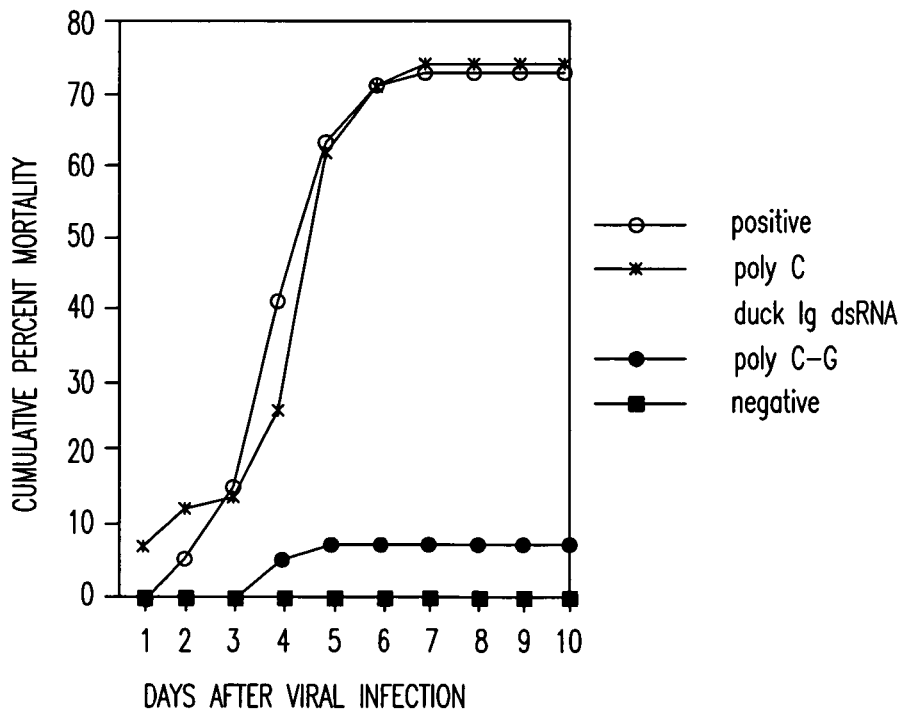

FIG. 8. Poly C-G, but not poly I-C or poly C induces the antiviral state. Shrimp (1-2 g, n=38-42) were injected with 8 μg (panel a) or 7 μg (panel b) of synthetic dsRNA analogues as indicated, and 72 hours later infected with WSSV. All RNA analogues were purchased from Sigma-Aldrich, re-constituted in 400 mM NaCl, 10 mM Tris-Cl, pH 7.4, and annealed and quantified as described in the Materials and Methods infra. dsRNA for the duck υ. (7 μg) was included in the experiment on panel b for comparison. The chi-square statistic was used to assess the significance of the observed antiviral protection, relative to positive controls: panel a) poly CG ($\chi^2$=16.92, p<0.001); panel b) duck Igυ dsRNA ($\chi^2$=32.17, p<0.001; poly CG ($\chi^2$=35.05, p<0.001).

Figure 9A:
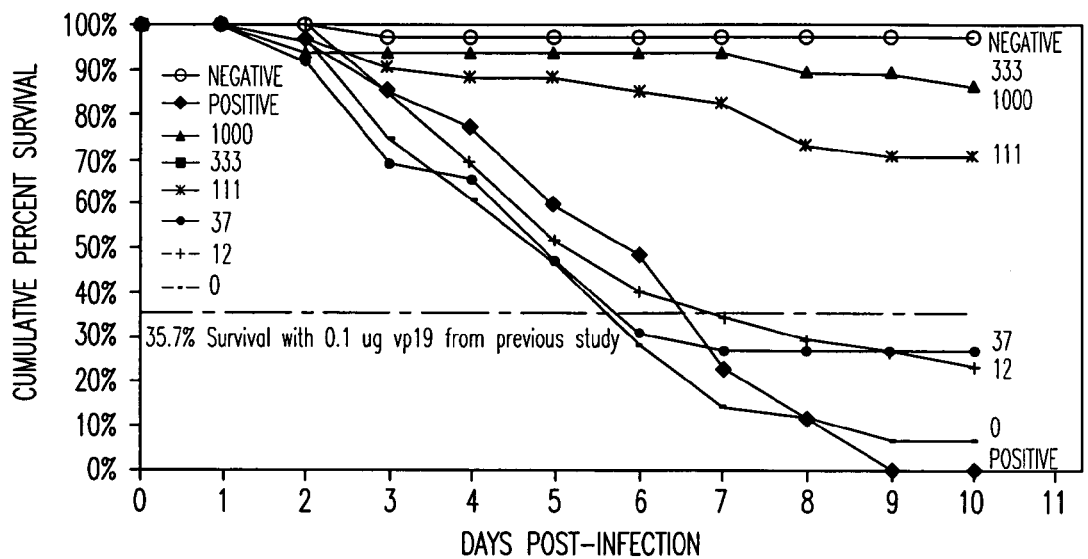
Figure 9B:
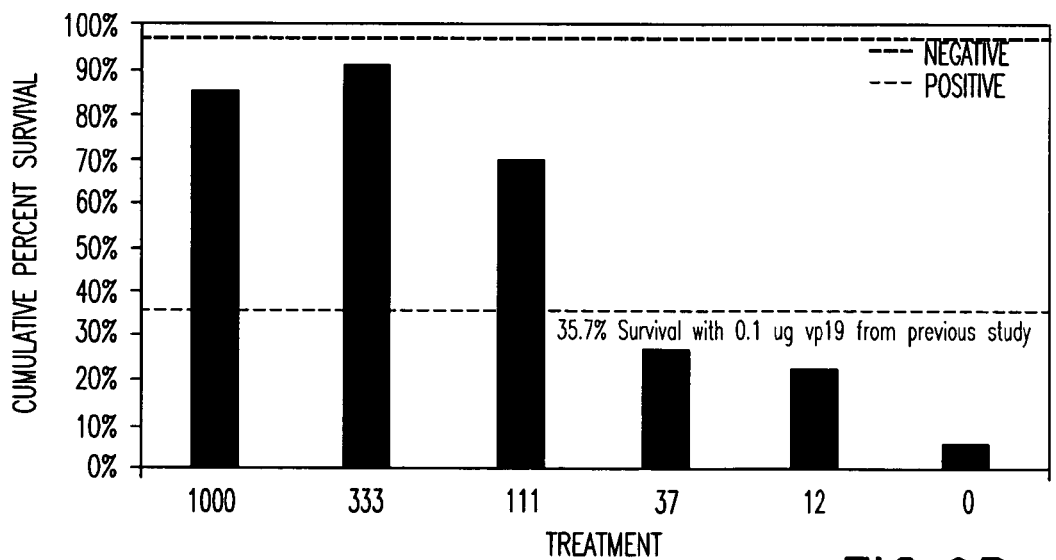

FIG. 9 contains the results of an experiment which shows that addition of polyC:G to vp19 dsRNA enhances the level of protection seen against WSSV infection.

Figure 10:
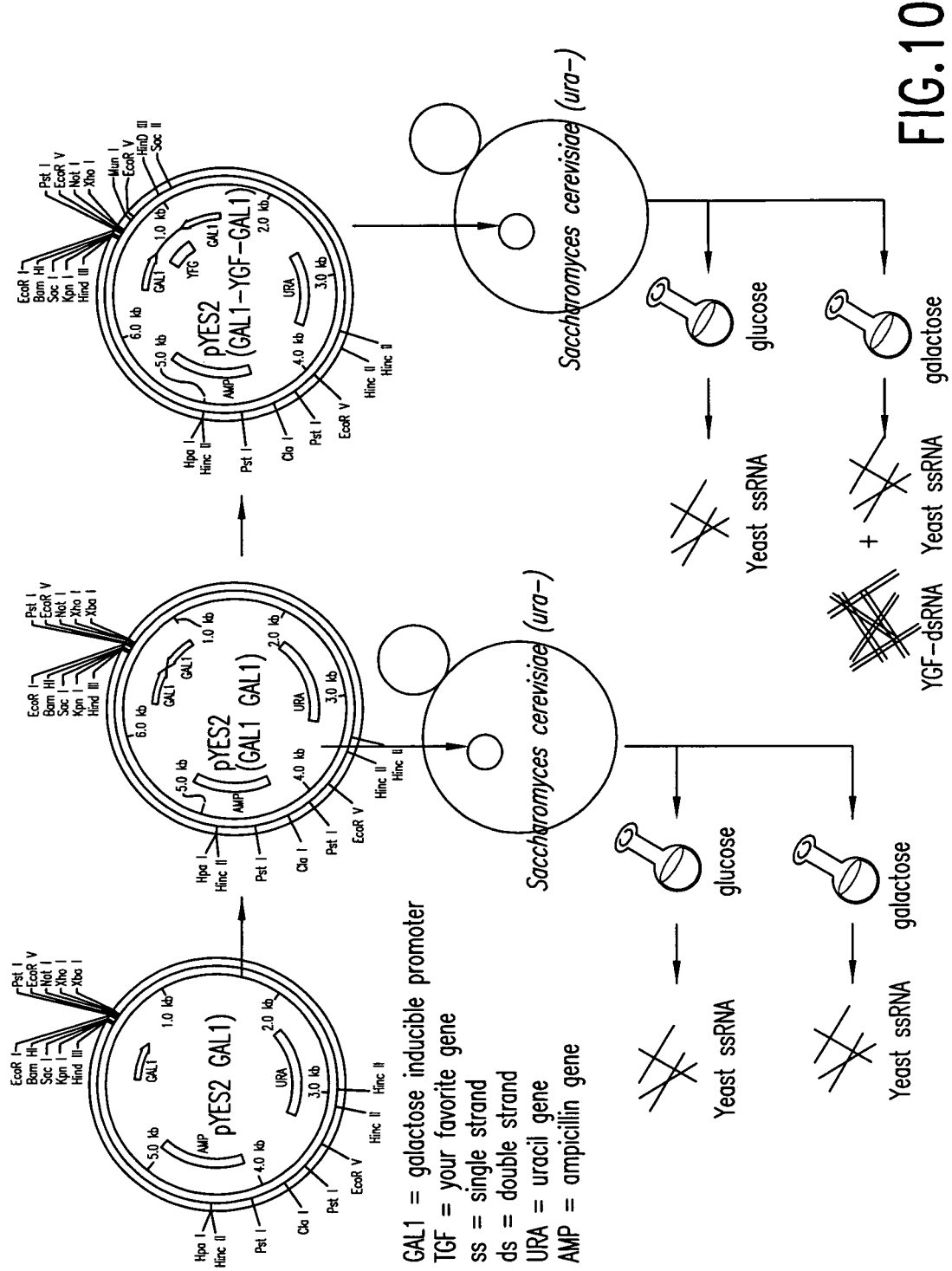

FIG. 10 schematically depicts construction of a vector that contains a dsRNA expressed under the regulatory control of an inducible (galactose) promoter, selectable markers (URA, AMP) and a desired gene, the introduction of said vector into *Saccharomyces* yeast, followed by selection and expression of the gene and dsRNA under galactose induction conditions.

Figure 11:
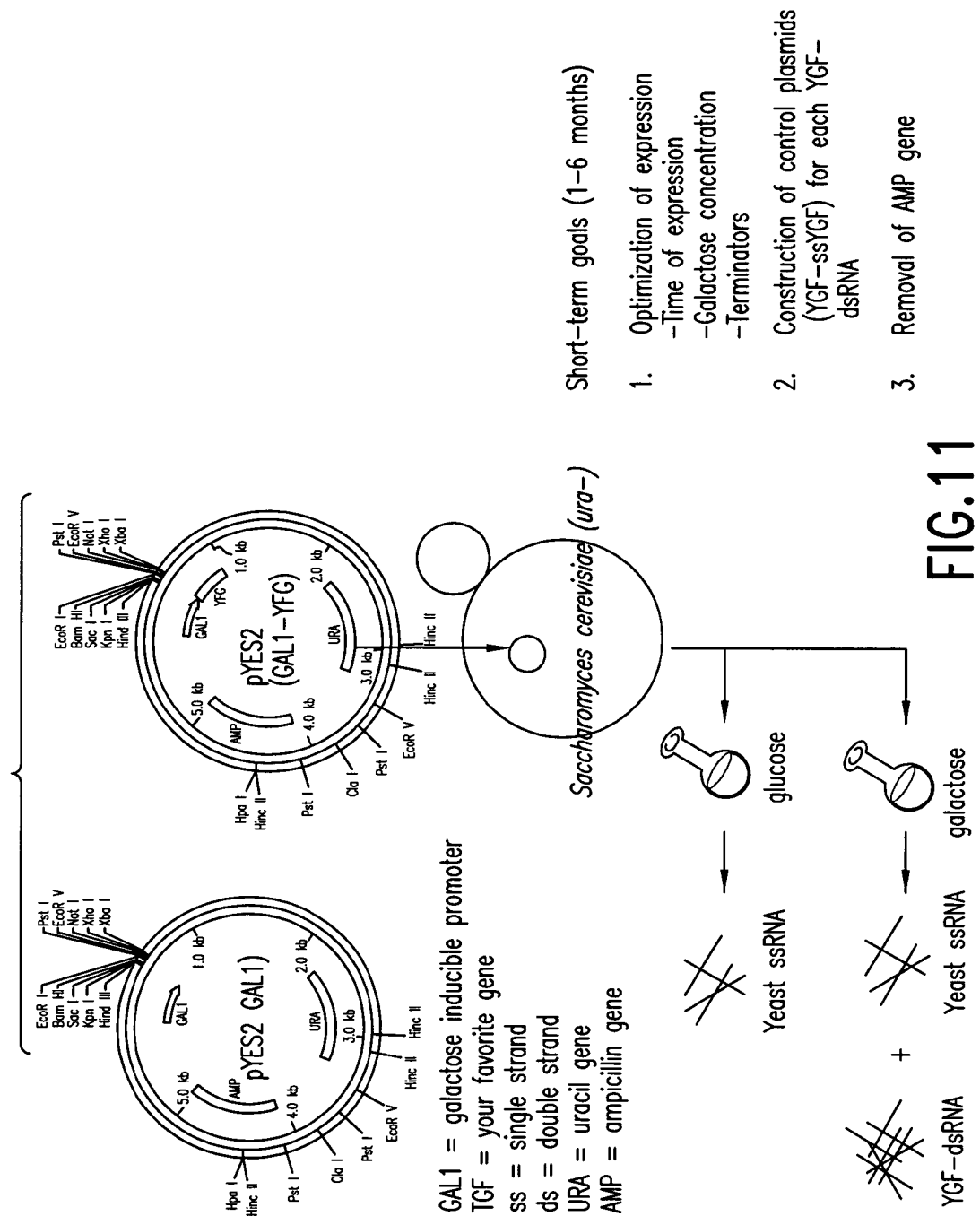

FIG. 11 depicts schematically introduction of a yeast expression vector as depicted in FIG. 8 into *Saccharomyces* cells, and selection of optimized expression conditions, timing of expression, galactose concentration, and terminators, construction of control plasmids, and removal of AMP gene.

Figures 12A, 12B, 12C:
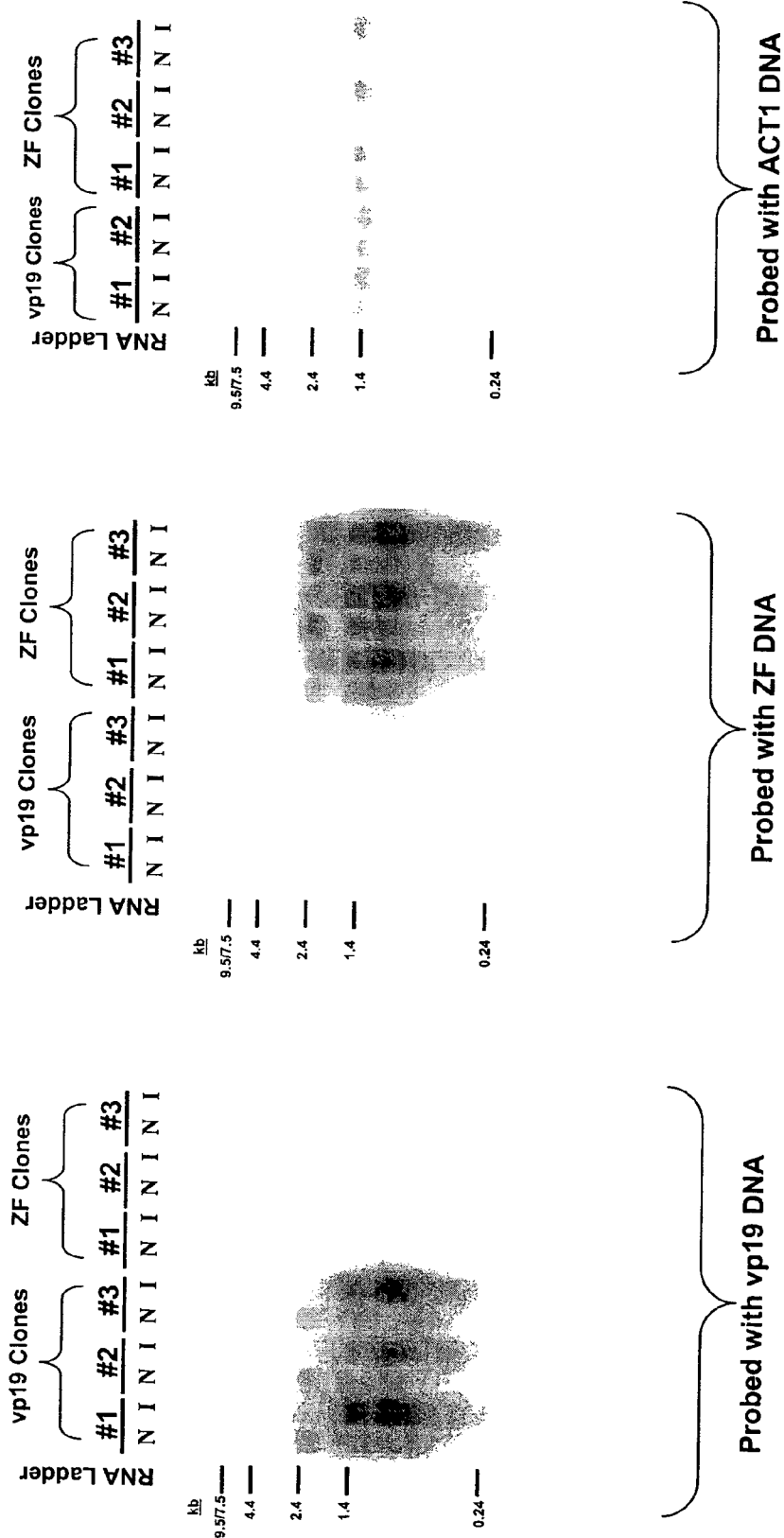

FIG. 12 depicts results of Northern analyses which demonstrate that Saccharomyces yeast express WSSV-encoded RNA when transformed with vectors containing vp19 or ZF sequences of WSSV. In these experiments, micrograms of total RNA extracted from transformed yeast were analyzed by Northern Blot, using probes specific for Vp19, ZF or yeast actin as a positive control. The results demonstrate that yeast express WSSV-related RNA.

Figures 13A, 13B:
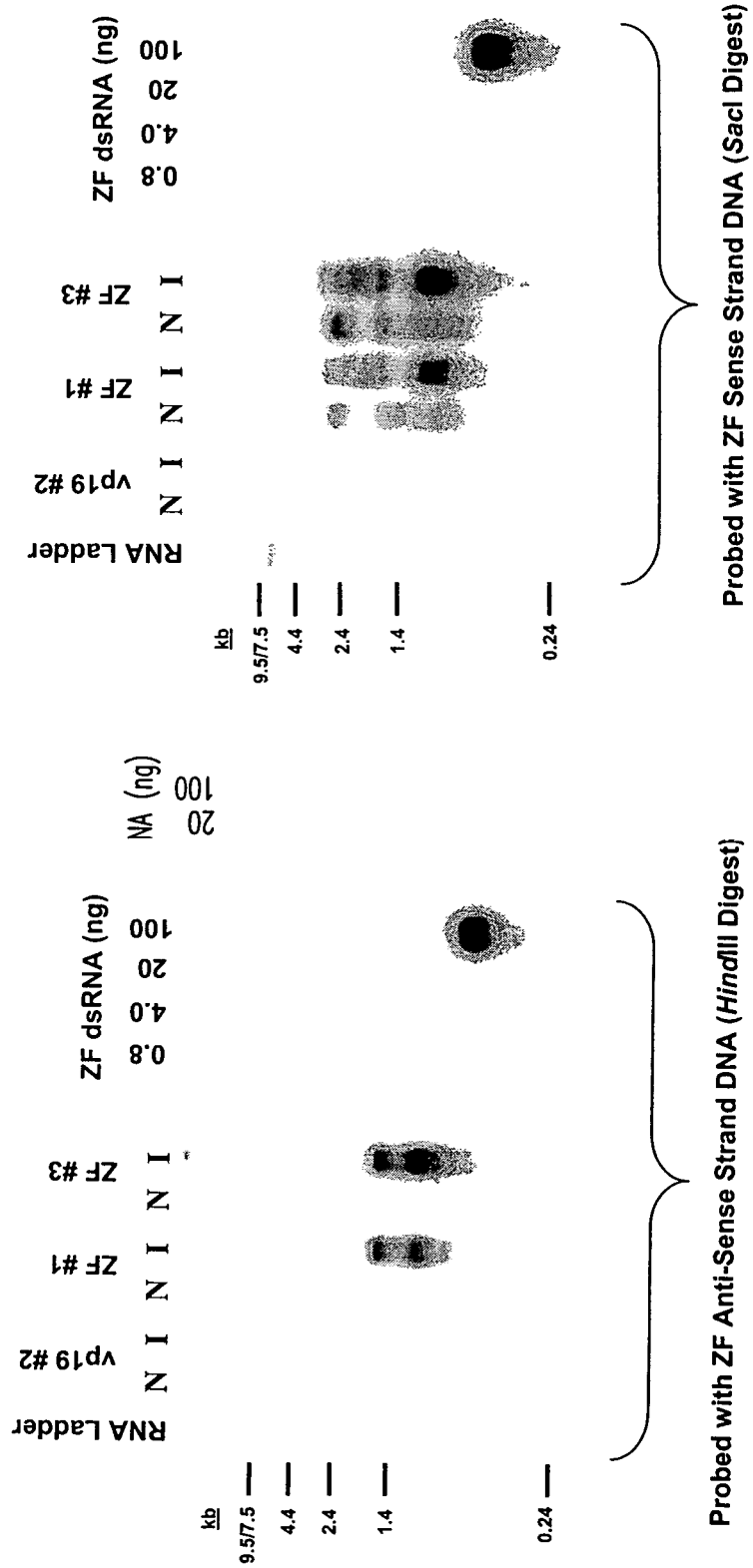

FIG. 13 shows Northern Blot analysis results which demonstrate that yeast transformed with a dsRNA vector according to the invention express dsRNA (when transformed with vectors containing ZF sequences). In these experiments, 10 micrograms of total RNA extracted from yeast transformed with a ZF-expressing vector were analyzed by Northern Blot. Probes specific for each strand (anti-sense, left and sense, right) were used, and as evidenced by the Northern Blot results, both detected their respective targets, confirming that dsRNA specific to ZF was expressed. Additionally, the standards (to the right of each gel) allow for the approximation of the amount of WSSV ZF RNA (approximately 50 nanograms) that are present in each RNA sample.

DETAILED DESCRIPTION OF THE INVENTION

Prior to describing the invention in more detail, the following definitions are provided. Otherwise, all terms and phrases are to be construed as they would be by a person skilled in the relevant art.

The present invention employs compounds, particularly dsRNA, oligonucleotides and modified derivatives thereof for use in modulating the function or effect of nucleic acid molecules encoding a target gene. This is accomplished by providing a dsRNA which specifically hybridizes with one or more nucleic acid molecules encoding said target gene or a long dsRNA (50 or so nucleotides, preferably 100 nucleotides or longer) that may or may not comprise a region that is homologous to any target gene and which elicits a generic immune response. As used herein, the terms "target nucleic acid" and "nucleic acid molecule encoding a target gene" have been used for convenience to encompass DNA encoding the gene including pre-mRNA and mRNA (or portions thereof) transcribed from such DNA, and also cDNA derived from such RNA.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of the target gene. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances, e.g., high, low and moderate stringency conditions.

An example of "low stringency conditions" is that two nucleic acid sequences hybridize in 10% formamide 5 times Denhardt's Solution, 6×SSPE, 0.2% SDS at 42° C.

Moderate Stringency Condition" means that hybridization occurs in 50% formamide, 5× Denhardt's soluction, 5×SSPE, 0.2% SDS at 42° C., followed by washing in 0.2×SSPE, 0.2% SDS at 65° C.

"High Stringency Conditions" means that hybridization occurs in 50% formamide, 5× Dehhardt's solution, 5×SSPE, 0.2% SDS at 42° C., followed by washing in 0.1×SSPE, and 0.1% SDS at 65° C.

A dsRNA compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

A "non-specific" or "non-sequence specific" dsRNA refers to a dsRNA that does not possess any significant known sequence identity to that of the genome of the invertebrate to which it is administered or to a parasite that infects said invertebrate, e.g., a marine invertebrate such as a crustacean, mollusk, preferably a shrimp. An example is poly C:G. Preferably the "non-specific dsRNA" will be long, i.e., at keast 50 nucleotides, more preferably at least 200-500 nucleotides or longer. In preferred embodiments the dsRNA will have the capability of promoting (enhancing) RNA interference response elicited by a sequence-specific dsRNA that targets (inhibits) the expression of a particular target gene, e.g., a crustacean gene or an essential gene of a parasite that infects a crustacean.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. Exemplary stringent hybridization conditions are provided supra.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of a dsRNA according to the invention need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the dsRNA of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, a dsRNA compound in which 18 of 20 nucleobases of the compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, a dsRNA compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

In the context of this invention, the term "oligomeric compound" or "oligomeric nucleic acid molecule" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While dsRNA oligonucleotides are a preferred form of the compounds of this invention, the present invention encompasses oligonucleotide analogs and mimetics modifications thereof as described below.

"Targeting" a dsRNA compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or preferably a nucleic acid molecule from an infectious agent. (e.g. virus)

The targeting process usually also includes determination of at least one target region, segment, or site within the target nucleic acid for a binding interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any- one -of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess. more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are herein below referred to as "preferred target segments." As used herein the term "preferred target segment" is defined as at least an 8-nucleobase portion of a target region to which a dsRNA compound is targeted. While not wishing to be bound by theory, it is presently believed that these target segments represent portions of the target nucleic acid which are accessible for hybridization.

While the specific sequences of several preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well. Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

The double-stranded RNA compounds of the invention may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Specific examples of modified dsRNA compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which are herein incorporated by reference.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which are herein incorporated by reference.

Alternatively, oligonucleotide mimetics wherein both the sugar and the internucleoside linkage (i.e. the backbone), of some nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

For example, dsRNAs according to the invention, may comprise oligonucleotides with phosphorothioate backbones and oligonucleosides with heteroatom backbones, and in particular —CH2-NH—O—CH2-, —CH2-N(CH3)-O—CH2- [known as a methylene (methylimino) or MMI backbone], —CH2-O—N(CH2)—CH.sub.2-, —CH2-N(CH3)-N(CH3)-CH2- and —O—N(CH3)-CH2-CH2- [wherein the native phosphodiester backbone is represented as —O—P—O—CH2-] of the above referenced U.S. Pat. No. 5,489,677, the amide backbones of the above referenced U.S. Pat. No. 5,602,240, and oligonucleotides having morpholino backbone structures as disclosed in U.S. Pat. No. 5,034,506.

Additionally, modified oligonucleotides, according to the invention, may also contain one or more substituted sugar moieties. For example, oligonucleotides may comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl, more particularly O[(CH2)nO]mCH3 O(CH2)nOCH3, O(CH2)nNH2, O(CH2)nCH3, O(CH2)nONH2 and O(CH2)nON[(CH2)nCH3]2, where n and m are from 1 to about 10. Additionally, preferred oligonucleotides comprise one of the following at the 2' position: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3 OCF3 SOCH3 SO2CH3 ONO2 NO2 N3 NH2 heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

Other potential modifications include 2'-methoxy (2'-O—CH3), 2'-aminopropoxy (2'-OCH2CH2CH2NH2), 2'-allyl (2'-CH2-CH=CH2), 2'-O-allyl (2'-O—CH2-CH=CH2) and 2'-fluoro (2'-F). The 2'-modification may be in the arabino (up) position or ribo (down) position. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Another potential modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methelyne (—CH2)n group bridging the 2' oxygen atom and the 4' carbon atom wherein n is 1 or 2. LNAs and preparation thereof are described in WO 98/39352 and WO 99/14226.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-amino-adenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazi-n-2(3H)-one), phenothiazine cytidine (1H-pyrimido[5,4-b][1,4]benzothiazin-2(3H)-one), a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5] pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, each of which is herein incorporated by reference.

Additionally, the oligonucleotides of the invention may be chemically linked to one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

The dsRNA compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,530,575; and 5,595;756, each of which is herein incorporated by reference.

The compounds of the invention further encompass any biologically acceptable salts, esters, or salts of such esters, or any other compound which, upon administration to an invertebrate, is capable of providing (directly or indirectly) the biologically active metabolite or residue thereof.

The term "biologically acceptable salts" refers to physiologically and pharmaceutically acceptable salts of the compounds of the invention: i.e., salts that retain the desired biological activity of the parent compound and do not impart undesired toxicological effects thereto.

The present invention also includes biological compositions and formulations which include the dsRNA compounds of the invention. The pharmaceutical compositions of the present invention may be administered in a number of ways depending upon whether local or systemic treatment is desired and upon the area to be treated. Administration may be topical, oral or parenteral. Parenteral administration includes injection or infusion.

In the context of the invention, "co-administration" means the administration of two different compounds, preferably dsRNAs, separately or in combination, and in either order. Preferably such dsRNAs may be comprised in biodelivery vehicles as described infra.

The dsRNA formulations of the present invention include, but are not limited to, solutions, emulsions, foams and liposome-containing formulations. The pharmaceutical compositions of the present invention may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged nucleic acid molecules to form a stable complex. Liposomes that are pH-sensitive or negatively-charged are believed to entrap nucleic acid molecules rather than complex with it. Both cationic and noncationic liposomes have been used to deliver nucleic acid to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

The dsRNA formulations of the invention may employ the use of various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposoines, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable.

Compositions and formulations for parenteral, administration may include sterile aqueous solutions which may also contain buffers, diluents and other suitable additives such as, but not limited to, penetration enhancers, carrier compounds and other pharmaceutically acceptable carriers or excipients.

Additionally, the dsRNA compositions of the invention may contain more than one dsRNA compound, e.g., a first dsRNA targeted to a first nucleic acid and one or more additional dsRNA compounds targeted to a second nucleic acid target, or non-targeted dsRNA (a sequence having no known homology to a target gene). Also, compositions of the invention may contain two or more dsRNA compounds targeted to different regions of the same nucleic acid target. Two or more combined compounds may be used together or sequentially.

The discovery that dsRNAs induce an immune response in at least marine invertebrates such as crustaceans and most probably other invertebrates has its origins in experiments designed to gain a greater understanding of invertebrate immunity and more particularly an understanding of genes and pathways that regulate crustacean gene expression and immunity and also experiments designed with the idea of potentially inducing sequence specific immune responses in shrimp as a means of providing protection against viral pathogens that normally infect shrimp, e.g., White Spot Syndrome Virus (WSSV), Taura Syndrome Virus (TSV) Infectious hypodermal and hematopoietic necrosis virus (IHHNV), Baculovirus of penaeid shrimp (BP), Rhabdovirus of penaeid shrimp (RPS), Gill-associated virus (GAV), Yellow head virus (YHV), Lymphoid organ-associated virus (LOVV), Lymphoidal parvolike viral disease (LPV), Hepatopancreatic parvovirus (HPV), Baculoviral midgut gland necrosis virus (BMN), Monodon baculovirus (MBV) Reo like virus diseases (REO), Rhabdovirus (RPS) and emerging viruses.

Specifically, the inventors conducted experiments to assess the role of various genes contained in several viruses that normally infect crustaceans, particularly shrimp, by the synthesis and administration of dsRNAs that correspond to target genes in shrimp viruses, particularly i.e., WSSV and TSV. Also, the inventors conducted experiments to evaluate whether specific shrimp genes, putative components of the NFKB and STAT signaling pathways, and other endogenous genes could be modulated (inhibited) by the administration of dsRNAs having sequences that correspond to genes putatively involved in shrimp immunity. Further, the inventors conducted experiments to assess the feasibility of particular biodelivery vehicles particularly yeast as a means for introducing dsRNAs into crustaceans.

The inventors specifically studied the effect of dsRNAs targeting the expression of the envelope protein VP28 and other selected genes in WSSV in the systemic infection process. The VP28 gene was initially selected because VP28 is thought to be anchored to the envelope of WSSV by a putative transmembrane domain, with the remainder of the polypeptide exposed on the outside of the viral particle. This theory, based on the primary structure of VP28, is supported by the observation that treatment of infectious WSSV preparations with VP28 antibodies prevents their potency when injected into L. vannamei. Thus, the expression of this gene is essential to the ability of WSSV to infect crustaceans, i.e. shrimp.

However, this gene is exemplary as the invention broadly encompasses the use of dsRNA to specifically or systemically modulate endogenous gene expression or essential genes comprised in other marine invertebrates and invertebrate parasites, preferably crustacean parasites, e.g., dsRNAs corresponding to crustacean genes involved in immunity, growth, reproduction, and general health or robustness, such as STAT, IKB and other putative components of the NFKB and STAT signaling pathways. Such genes also include those coding for neurotransmitters, hormones and metabolic pathways which include molt inhibiting hormone, gonad inhibiting hormone and crustacean hyperglycemic hormone. Such genes also include those coding for antimicrobials or regulators for production of such peptides which include crustins and penaeidins. Potentially dsRNA can be used to downregulate the expression of any desired marine invertebrate, e.g., crustacean gene. For example, putative target genes can be identified in genomic libraries, e.g., suppression subtractive hybridization libraries generated using control and viral (WSSV or TSV) infected shrimp tissues. Other specific examples of potential target genes include VP28, ribonucleotide reductase, hemocyanin, VP26, VP19, thymidylate kinase, and DNA polymerase.

Particularly, the inventors initially conducted experiments to study the possible antiviral effects of the injection of dsRNAs corresponding to WSSV and shrimp expressed genes identified in a L. vannemei EST collection that includes subtractive hybridization libraries (PCR Select, Clontech) prepared from WSSV challenge experiments. These experiments included the construction and injection of dsRNAs corresponding to the shrimp IKBK gene, STAT gene, and hemocyanin gene, and the WSSV VP28, ribonucleotide reductase small subunit, and DNA polymerase gene, as well as a control dsRNA (to assess the possible sequence-independent effects of dsRNA) encoding a portion of the immunoglobulin □ of the duck, Anas platyrhynchos.

The results of these dsRNA studies [discussed in detail in the examples] have shown, for the first time, that treatment of a crustacean, i.e., a shrimp, with dsRNA corresponding to a gene contained in a viral pathogen (WSSV) effectively protects said shrimp against viral (WSSV) infection. Also, these dsRNA studies have further established that target endogenous shrimp genes (hemocyanin, STAT and IKappa B Kinase catalytic subunit) are down-regulated in a sequence-specific manner by the administration of dsRNAs that target said genes. The sequence-specificity of down-regulation was revealed by the unaffected expression of a control gene (ribosomal protein mRNA) in all dsRNA-treated shrimp, and by the normal expression of IKBK mRNA in STAT dsRNA-treated animals, and vice-versa.

These experimental results for the first time demonstrate the existence of an RNAi pathway in shrimp, and establish the feasibility of antiviral strategies using dsRNA-related therapeutics in marine invertebrate aquaculture, e.g., crustacean aquaculture. This discovery has great commercial significance because more than 20 pathogenic viruses are known to infect shrimp species and cause great economic losses to shrimp aquaculture worldwide. Therefore, viable antiviral strategies for eradicating or alleviating such shrimp pathogenic viruses is of great potential commercial importance (as viral-related shrimp losses run in the billions of dollars annually).

However, as noted supra, the inventors also had a broader goal in these dsRNA studies; particularly they wanted to gain a greater understanding of the immune system of invertebrates, e.g., crustaceans by the study of the marine shrimp, *Litopenaeus vannamei*, and the effect of dsRNA as that response to infection by two viruses, Taura Syndrome Virus (TSV) and White Spot Syndrome Virus (WSSV).

The rationale for these studies was based in part on the following observations: 1) crustaceans are essential components of the marine (especially coastal) environment; 2) certain crustacean species, especially marine shrimp, are of commercial significance and are widely aquacultured; 3) crustaceans are highly susceptible to numerous viral infections, which have devastating effects on aquaculture and cause unknown environmental consequences, and 4) very little is known about crustacean immune reaction to viruses.

Because so little was known about crustacean immunity prior to the invention, the inventors used functional genomic approaches to rapidly obtain genetic information on shrimp genes of potential importance in eliciting immune reactions in shrimp. Particularly, based on the results of functional genomic studies, two genes were selected for study, a STAT-like gene and an I-KB-Kinase-like gene (IKK), as the focus of RNAi studies conducted with the goal of identifying the immune function of these genes. These genes were selected because of the known role of putative orthologs thereof in signal transduction pathways of great importance to immune responses in other animals, e.g., mammals and insects.

Based on their sequences, it was hypothesized that these two shrimp genes are orthologs of a STAT-like family member and a catalytic subunit of the IKB kinase complex, expressed in vertebrates, that encode components of the shrimp immune response, and more specifically a component of the shrimp antiviral response. In order to test this hypothesis, RNA interference experiments were conducted to potentially knock down the expression of these genes in order to dissect the effect on shrimp immune physiology and resistance to viral infection. Whether gene expression would be knocked down was not predictable because it was not then known whether crustaceans were even capable of responding to dsRNA via RNA interference pathways.

The results of these dsRNA experiments indicated that these endogenous shrimp STAT and IKBK genes were effectively down-regulated by the administration of dsRNAs in a sequence-specific manner. While this down-regulation was not complete as traces of both STAT and IKBK mRNAs were detectable by RT-PCR, these results demonstrated for the first time that interfering RNAs can be used in crustacean systems, and shrimp particularly, as a means of studying and knocking down the function of specific crustacean genes, e.g., genes that are putatively involved in innate immune responses. Also, these results demonstrate that RNA interference can be used to produce marine invertebrates such as crustaceans, e.g., shrimp, that have impaired or deleted expression of an endogenous gene.

Additionally, and quite unexpectedly, these experiments indicated that the administration of at least one long double stranded RNA, i.e., longer than 21-25 nucleotides, preferably 50 nucleotides or longer, which does not possess a sequence having known homology to any endogenous shrimp or shrimp virus genes resulted in the induction of a systemic immune response which conferred generic protection against different viral pathogens, i.e., an immune response conferring protection against different pathogens. In other words, the dsRNA conferred generic protection against different pathogens in a non-sequence specific manner.

Also unexpectedly, other experiments demonstrated that the co-administration of a long non-specific dsRNA (e.g., poly C:G) and a sequence-specific dsRNA (e.g., one that modulates expression of a target gene containing a homologous sequence), potentiates the RNAi response elicited by the sequence-specific dsRNA. This is advantageous in that it should enable the administration of reduced concentrations of sequence-specific dsRNAs while still eliciting the desired gene modulatory response. Such benefit is of significant commercial importance given the great expense associated with synthesizing desired dsRNAs. Also, this discovery is beneficial as it may result in more long-lived RNAi responses.

The systemic antiviral effects of dsRNA in invertebrates, e.g., shrimp were initially observed during RNA interference studies of the immune response of the marine shrimp, *Litopenaeus vannamei*, when dsRNAs representing selected shrimp and viral genes and genes which were non-specific controls (e.g., duck immunoglobulin gene) were injected and the animals subjected to viral challenge. Entirely unexpectedly, it was observed that the injection of any dsRNA, i.e., not only dsRNAs specific to a target viral or host gene, but also dsRNA having no homology to any known crustacean or viral gene, resulted in increased survival challenge to Taura Syndrome Virus (TSV) or White Spot Syndrome Virus (WSSV). These results were quite surprising because, while vertebrates are known to mount a strong innate immune response against viral infections, largely by the activation of the interferon system by dsRNAs, no general inducible antiviral defense mechanism similar to vertebrate interferon has ever been seen or even speculated to exist in invertebrates. The results of the present invention suggest that dsRNA is an ancient elicitor of antiviral immunity and that dsRNAs can elicit systemic immunity in invertebrates, and particularly crustaceans such as shrimp.

More particularly, the antiviral responses in *L. vannamei* against TSV and WSSV were compared after the administration of dsRNAs specific to target viral genes and dsRNAs not specific to any known target viral or host genes. It was observed that a dsRNA encoding a portion of the immunoglobulin υ heavy chain of duck, *Anas platyrhyncos*, having no known homology to any shrimp, TSV or WSSV gene induced an immune response against both TSV and WSSV. By contrast, dsDNAs and singled stranded RNAs (poly C) did not elicit such a response or confer antiviral protection. In order to confirm the validity of the existence of this systemic non-sequence specific response to dsRNA, the inventors further administered dsRNAs corresponding to a variety of vertebrate immunoglobulin genes (duck υ, pig γ), fish non-coding genomic DNA, bacterial vector sequences, and synthetic dsRNAs.

Again surprisingly, it was observed that all of these dsRNAs induced a protective antiviral response. By contrast, poly IC (dsRNA with inosine bases paired to cytosines), dsDNA and ssRNA (poly C), and RNase-treated dsRNA did not confer any viral protection. The failure of poly IC to induce viral protection in shrimp suggests that the immune mechanisms in invertebrates that elicit a recognition and immune response to dsRNAs, differ from those in vertebrates. It is hypothesized based on these results that invertebrates e.g., crustaceans, elicit an innate immune response against dsRNA by a dsRNA mediated immune response which is similar to that present in vertebrates, but which possesses fundamental differences.

The observed similarities include that 1) it is active against different viruses and 2) it is triggered by dsRNA in a sequence-independent manner. At least one significant difference is that the immune response observed in a crustacean system does not appear to involve an interferon system.

Specifically, in vertebrates dsRNA is recognized by Toll-like receptor 3 (TLR-3) which activates the interferon system, at least in part through the interferon B promoter. Ultimately, this interferon response results in the induction of hundreds of genes, some having antiviral activity, others regulating cell growth and modulating adaptive immune response. In mammals, dsRNA also binds to and directly activates the RNA-dependent protein kinase (PKR), which results in the inhibition of protein synthesis via phosphorylation of eukaryotic translation initial factor 2α eIF2α). However, invertebrates do not possess an interferon immune system. Therefore, the immune response elicited in crustaceans against dsRNAs must involve a different immune regulatory system, yet to be fully understood.

The discovery that marine invertebrates such as crustaceans, e.g., shrimp, and most probably other invertebrates respond to the administration of dsRNA via both sequence-specific and non-sequence specific (systemic immune response) mechanisms has important applications both for basic research and effective strategies for disease control in marine, e.g., shrimp aquaculture. Particularly dsRNAs specific to target genes can be used in molecular genetic studies as a reverse genetics tool in shrimp, e.g., in the study of reproductive biology and immunology. Furthermore, the development of technologies using dsRNA based antiviral therapies will facilitate new means of alleviating diseases and pathogens of shrimp and other crustaceans, particularly viral, bacterial, fungi, microsporidian, haplosporidian and gregarine pathogens. Also, dsRNAs can be administered as a means of inducing a systemic protective immune response, e.g. against virus or other invertebrate pathogens.

Thus, based on the foregoing, the present invention is broadly directed to the use of dsRNAs for inducing a systemic, non-sequence specific immune response and/or for inducing a sequence-specific gene expression modulating (inhibiting) immune response in an invertebrate, e.g., a marine invertebrate such as a mollusk or a crustacean, preferably a shrimp.

Also, the invention is broadly directed to the use of a non-sequence specific dsRNA, typically a long dsRNA to enhance the response elicited by a sequence-specific dsRNA by co-administration.

In general, the invention methods will include the administration or co-administration of an amount of at least one dsRNA, or a cocktail of dsRNAs, e.g., which are complementary or hybridize to a target gene sequence, and which preferably are at least about 21-25 nucleotides long or which exhibit no known homology to a target gene, and which preferably are at least 50-100 nucleotides long, and which optionally may comprise modified nucleotides, in an amount sufficient to elicit a protective RNAi and/or immune response against a particular disease or pathogen, e.g., a virus, bacterium, mycoplasma or fungus. As discussed, one novel aspect of this invention is that a dsRNA of sufficient size does not need to possess a sequence having sequence homology to any host gene or pathogen gene in order to elicit a systemic protective immune response or to potentiate a specific RNA interference elicited by a sequence specific dsRNA. Therefore, the administered non-specific dsRNA may be derived from any source, e.g., a virus, bacterium, or other invertebrate source, or from a vertebrate, e.g., mammal, amphibian, avian, reptile from a plant source, or it may be a synthetic dsRNA, e g., a homopolymer or heteropolymer of desired nucleotides. In the examples, it has been demonstrated that bacterial, synthetic, and different vertebrate dsRNAs all elicit in shrimp a systemic immune response, and that a non-specific dsRNA (poly C:G) potentiates the RNAi response elicited by a sequence specific (WSSV) dsRNA.

An administered dsRNA which elicits non-specific immune response is preferably a long dsRNA, i.e., preferably at least 50 nucleotides in length, more preferably at least 100-500 nucleotides, 1000-5000 nucleotides, with no known upper limit. An example thereof is poly C:G or another similar polymer of natural or modified nucleotides. By contrast, a dsRNA which elicits a sequence-specific response (down-regulation of gene corresponding to target gene) may be as short as 21-25 nucleotides, or longer if desired.

An administered dsRNA which elicits a sequence-specific RNAi response, preferably in a crustacean or other marine invertebrate will comprise a sequence that is identified or which exhibits substantial sequence identity with a target gene, e.g., at least 70%-80%, more preferably at least 80-90%, or at least 90-95% such that it specifically hybridizes with a target gene, e.g., an endogenous crustacean gene or a gene comprised in a parasite that infects crustacean and modulates, preferably inhibits or blocks the expression thereof. Preferably modulation of the expression of the target gene will confer a desired phenotypic effect or confer immunity against a particular pathogen. Preferably, the sequence specific dsRNA will comprise substantial homology as described above to a target gene identified in this application or more specifically to a nucleic acid sequence specifically identified herein.

A dsRNA will be administered in an amount sufficient to confer non-sequence specific immune response or a sequence-specific gene down-regulation, e.g., a dosage ranging from at least about 0.0001 mg to 0.001 mg more preferably at least about 0.001 to 0.01 mg and still more preferably at least about 0.1 mg to 0.5 mg with no known upper limit. It has been observed that as much as 100 μg of dsRNA injected into shrimp causes no toxicity. The mode of administration will be any means that results in a protective immune response. For example, the dsRNA may be injected (intravenously, subcutaneously, intramuscularly, etc.), it may be administered orally, it may be delivered via immersion, or transdermally. Physical methods include injection directly into host cells or extracelluar injection into an invertebrate, e.g., in the tail of a shrimp.

A particularly preferred means of delivery is a biodelivery system, e.g., yeast or, microalgae or other microbial cell that is ingestible by a crustacean and which expresses a desired dsRNA, e.g., one specific to a gene of a virus that infects crustaceans. For example, *Saccharomyces* may be transformed with a vector that expresses a dsRNA that targets a WSSV or TSV gene. Similarly, the genome of a microalgae such as *Chlamydomonas, Chlorella, Arthrospira (Spirulina), Haematococcus, Nannochloropsis, Skeletonema, Chaetocerus, Tetraselmis* or *Isochrysis* may be transformed with a vector that confers the expression of dsRNA therein. (See, Sineshchekar et al., Proc. Natl. Acad. Sci., USA 99(13):86889-97 (Jun. 25, 2002); Koblenz et al., J. Cell Sci. 116 (Pt. 13):2635-46 (July, 2003)). The dsRNA will be delivered by the crustacean or other invertebrate ingesting the microbia contained in a food or introduced into a culture media, or alternatively may be absorbed by the crustacean if the dsRNA is secreted into the culture media by the biodelivery vehicle. It is anticipated that ingestion of the biodelivery vehicle, e.g., yeast or microalgae, will facilitate the stability of the dsRNA (prevent it from being degraded by endogenous hydrolases) as it passes through the crustacean gut and provide for its introduction into the crustacean circulatory system thereby allowing for an immune response to be generated.

However, while biodelivery methods are preferred, the present invention embraces other delivery systems and compositions as earlier described.

The subject dsRNAs may be synthesized in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art. sup. 32,33,34 (see also WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

RNA may be directly introduced into the cell (i.e., intracellularly); or introduced extracellularly into a cavity, interstitial space, into the circulation of an organism, introduced orally, or may be introduced by bathing an organism in a solution containing the RNA. Methods for oral introduction include direct mixing of the RNA with food of the organism, as well as engineered approaches in which a species that is used as food (yeast or microalgae) is engineered to express the RNA, then fed to the organism to be affected. Alternatively, the crustacean or other marine invertebrate, may be immersed in fresh or salinated water containing the dsRNA(s). Physical methods of introducing nucleic acids, for example, injection directly into the cell or extracellular injection into the organism, may also be used. A transgenic organism that expresses RNA from a recombinant construct may be produced by introducing the construct into a zygote, an embryonic stem cell, or another multipotent cell derived from the crustacean animal.

Methods of engineering both yeast and microalgae to express heterologous genes are known in the art. However, prior the invention, the expression of a heterologous, introduced dsRNA in a yeast had not been known. With respect thereto, it was unknown whether yeast would be capable of stably expressing dsRNA at detectable levels. Expression of dsRNA is particularly complex, as dsRNA may be unstable in vivo (e.g. inside microorganisms), because cells typically express multiple nucleases as a mechanism of regulating nucleic acid metabolism, and gene expression, including the degradation of single strand RNA (ssRNA) and dsRNA. For instance, in the genome of S. cerevisiae 6 ribonucleases (such as Rpp1, Pan3, Pan2, Rnh1, Rnt1 and Rny1) are found to potentially degrade single and/or double strand RNA. In other microorganisms, such as E. coli, the degradation of ssRNA and dsRNA is also exerted by ribonucleases, but only the E. coli ribonuclease III is able to degrade dsRNA (Calin-Jageman and Nicholson 2003b; Calin-Jageman and Nicholson 2003a). Thus, in E. coli, expression of dsRNA can be achieved upon deletion of the ribonuclease III gene (Sun et al. 2001). Surprisingly, as evidenced by the results contained in the examples, Saccharomyces cells in which ribonuclease genes have not been altered express detectable levels of a dsRNA (WSSV dsRNA) under galactose inducible conditions. Thus, Saccharomyces or other yeast which are safely ingestible by crustaceans, such as shrimp, should provide a suitable means of delivery of dsRNA therein. Other examples of yeast known to be suitable for heterologous gene expression include Pichia, Yarrowia, Candida, Hansenula, Schizosaccharomyces, and the like.

In the example herein, a galactose inducible promoter was used to regulate dsRNA expression in Saccharomyces. However, any promoter that is functional in the particular host cell may be utilized. Examples of constitutive and regulatable promoters functional in yeast include PHO81, PHO2, PHO4, and other acid phosphotase and alkaline phosphatase inducible promoters, GLA1, GAL2, GAL4, GAL7, GAL10 and other galactose regulated promoters, phosphoglycerokinase promoter, and the like.

In a preferred embodiment, the yeast may be transformed or transfected with 2 different vectors encoding different dsRNAs so that the expression of different genes may be inhibited or in order to obtain additive or synergistive results attributable to administration of different dsRNAs specific to the same pathogen gene. While the invention is exemplified with a dsRNA specific to a WSSV gene, it is anticipated that yeast delivery systems may be used to deliver dsRNAs to other animals, e.g., other invertebrates, preferably other marine invertebrates.

Similarly, microalgae, when used as a biodelivery system, will be introduced into a feed, culture medium or contacted with a crustacean. It is anticipated that the microalgae will also act as a biostabifizer and allow a desired dsRNA to be stably delivered through the gut and into the target circulatory system, e.g., that of a crustacean, preferably a shrimp.

Means for introducing and vector for expressing heterologous nucleic acid sequences in microalgae are also well known in the art. (See, e.g., US 200400478281 published Mar. 11, 2004; US 20030022359 published Jan. 30, 2003; US 20030033626 published Feb. 13, 2003; US 20030186856 published Oct. 2, 2003 and US 20030211089 published Nov. 13, 2003, all incorporated by reference in their entirety).

See also, Sineshchekov et al., Proc. Natl. Acad. Sci., USA 99(131:8689-94 (Jun. 20, 2002); Koblenz et al., J. Cell Sci., 116 (pt. 13):2635-46 (2003), which teach expression of dsRNA in microalgae to knock down endogenous microalgae genes (rhodopsin, centrin genes) and Leona Banares et al., Trends Biotechnol. 22(i):43-52 (2004) which is a review of means for transformation of DNA in intero-microalgae. As with yeast, microalgae may be transformed to express one or several dsRNAs, which may be against specific target genes, e.g., viruses or may encode long dsRNAs that are non-specific and which induce a generic (systemic) immune response, e.g., generic antiviral immunity.

Physical methods of introducing nucleic acids further include injection of a solution containing the RNA, bombardment by particles covered by the RNA, soaking the cell or organism in a solution of the RNA, or electroporation of cell membranes in the presence of the RNA. A viral construct packaged into a viral particle will accomplish both efficient introduction of an expression construct into the cell and transcription of RNA encoded by the expression construct. Other methods known in the art for introducing nucleic acids to cells may be used, such as lipid-mediated carrier transport, liposomal delivery, chemical-mediated transport, such as calcium phosphate, attachment to carrier moieties, and the like. Thus the RNA may be introduced along with components that perform one or more of the following activities: enhance RNA uptake by the cell, promote annealing of the duplex strands, stabilize the annealed strands, or otherwise increase inhibition of the target gene.

While one important aspect of the invention is the discovery that dsRNAs of any sequence, preferably at least 50 nucleotides or longer, which may contain modified and non-naturally occurring nucleotides can be used to induce a systemic immune response in a crustacean, another important aspect of the invention relates to the administration of dsRNAs to crustaceans, e.g., shrimp, that possess sequences that are identical or which possess a high level of sequence identity with a targeted crustacean gene or a gene contained in a pathogen that normally infects a crustacean (in the administration of interfering RNAs having a sequence that target specific crustacean or pathogen genes). Preferably, the dsRNA will comprise a region of at least 21-25 nucleotides that is at least 70% preferably at least 80-90%, 95%, or greater sequence identity to a corresponding region of a target gene, e.g., viral or endogenous gene.

Specific examples thereof include dsRNAs corresponding to crustacean genes involved in immunity, growth, reproduction, and general health or "robustness" and essential genes of pathogens. Such genes include e.g., STAT, IKB and other putative components of the NFKB and STAT signaling pathways. Such genes also include those coding for neurotransmitters, hormones and metabolic pathways which include molt inhibiting hormone, gonad inhibiting hormone, crustacean hyperglycemic hormone. Such genes also include those coding for antimicrobials or regulators for production of such peptides which include crustins and penaeidins. Potentially dsRNA can be used to down-regulate the expression of any desired crustacean gene. For example, putative target genes can be identified in genomic libraries, e.g., suppression subtractive hybridization libraries generated using control and viral (WSSV or TSV) infected shrimp tissues. Other specific examples of potential target genes include VP28, ribonucleotide reductase, hemocyanin, VP26, VP19, thymidylate kinase, and DNA polymerase.

Preferably, the invention involves the administration of a dsRNA having a sequence that is identical or which exhibits high sequence identity, e.g., at least 75%, more preferably at least 85-90%, and more preferably from 90-99% identical to a crustacean gene or a gene of a pathogen that normally infects a crustacean. In the case of shrimp, such pathogens include viruses such as White spot syndrome virus, Taura syndrome virus, Infectious hypodermal and hematopoietic necrosis virus (IHHNV), Baculovirus of penaeid shrimp (BP), Rhabdovirus of penaeid shrimp (RPS), Gill-associated virus (GAV), Yellow head virus (YHV), Lymphoid organ-associated virus (LOVV), Lymphoidal parvolike viral disease (LPV), Hepatopancreatic parvovirus (HPV), Baculoviral midgut gland necrosis virus (BMN), Monodon baculovirus (MBV) Reo like virus diseases (REO), Rhabdovirus (RPS) and emerging viruses for which essential genes may be sequenced through any means available to those skilled in the art.

Bacterial pathogens that infect shrimp include *Vibrio* spp., *Micobacteria* spp., Necrotizing hepatopancreatitis (NHP) and rickettsia or rickettsial-like agents. Fungi that infect shrimp include *Fusarium oxysporum, Lagenidium* or *Sirolpidium*. Other parasites that infect shrimp include microsporidians, haplosporidians and gregarines.

The preferred dosage effective amounts of said sequence-specific dsRNA are the same as set forth above. The size of said sequence-specific dsRNA will range from at least 20 to 50,000 nucleotides in length, more preferably from about 20 nucleotides in length to about 5000 nucleotides in length, and more preferably from about 20 to 500 nucleotides in length.

RNA's specific to target genes can be used to down-regulate gene expression in any marine invertebrate, e.g., crustacean animal. Crustaceans include by way of example shrimp, crabs, crayfish, and lobster. Specific examples of shrimp include Akiami past shrimp, Baltic prawn, banana prawn, blue shrimp, brine shrimp, brown tiger prawn, caramote prawn, eastern king prawn, eastern school shrimp, fleshy prawn, freshwater prawns, shrimp, giant river prawn, giant tiger prawn, greasy back shrimp, green tiger prawn, Karuma prawn, metapenaeus shrimps, northern white shrimp, palemonid shrimps and whiteleg shrimp.

Specific examples of crab species encompassed by the invention include blue crab, Chinese river crab, gazami crab, Indo-Pacific shrimp crab, marine crabs, portunus swimcrabs, spinous spider crab and swimcrabs.

Specific examples of crayfish encompassed by the invention include Danube crayfish, Euro-American crayfishes, Maron crayfish, Noble crayfish, red claw crayfish, red swamp crayfish, signal crayfish, and yabby crayfish.

Finally, specific examples of lobster encompassed by the invention include flathead lobster, Japanese Spiny lobster, mud spiny lobster, Palinurid spiny lobsters, spiny lobsters, and tropical spiny lobsters.

In preferred embodiments of the invention, a crustacean, e.g., shrimp will be treated with a combination of a long dsRNA that induces non-specific (systemic) immunity and another dsRNA that inhibits the expression of a target gene in a sequence-specific manner by RNA interference.

In another preferred embodiment of the invention, a crustacean, e.g., a shrimp will be treated with at least one sequence-specific dsRNA and another non-specific dsRNA under control dosage conditions whereby said non-sequence specific dsRNA acts as an "adjuvant" and potentiates the RNAi response elicited by the sequence specific dsRNA on the expression of a gene that contains a sequence identical or substantially similar to a sequence comprised in the sequence specific dsRNA. Preferably, the amount of the non-specific dsRNA relative to sequence specific dsRNA will comprise an amount that potentiates the response elicited by the sequence specific dsRNA by at least 10-fold thereby enabling the dosage thereof to be diminished without compromise to efficacy.

Another significant aspect of the invention involves the use of functional genomics with RNA interference to identify crustacean genes involved in immune regulation and viral immunity. Such genes will be identified from known EST libraries or may be identified from novel libraries, e.g., libraries generated from crustacean animals infected with a virus, which consist of genes up-regulated or down-regulated by viral infection.

A preferred gene source is the EST library reported at www.marinegenomics.org which presently contains several thousand shrimp gene sequences and which is continually updated as more shrimp genes become known. The availability of these putative genes allows the design of dsRNAs that can be used to inhibit their expression and identify the function thereof. Preferably, the genes selected will be orthologs of immune regulatory genes expressed in other animals, e.g., mammals or insects. However, the invention broadly encompasses the use of RNA interference to ascertain the function of any target marine invertebrate, e.g., crustacean gene.

The function of the gene will be assessed e.g., by observing a phenotypic change, e.g., alterations in hemopoiesis, inflammation, growth, reproduction, differentiation, resistance to viral infection, color and the like when the gene is down-regulated by an interfering dsRNA. Ideally, the target gene expression will be inhibited by at least 80-90%, more preferably 95-99%. After a phenotypic change is observed, and gene function postulated, gene function can potentially be confirmed by the construction of transgenic crustaceans that lack and therefore do not express the particular target gene.

After the function of a target gene is identified, the gene or the corresponding gene product may itself be used as a target to identify compounds, e.g., antibodies, small molecules, nucleic acids and proteins that modulate (up or down-regulate) the expression thereof. In preferred embodiments, the target gene will be an immune regulatory gene and the compound will enhance immunity, e.g., elicit or promote antiviral immunity or disease resistance.

Microarray technology can be used to identify genes that are up-regulated or down-regulated in crustaceans, e.g., shrimp, under specific conditions, e.g., when exposed to dsRNA or virally infected, under stress conditions, nutrient deprivation, during embryogenesis and reproduction, and the like. Thereupon those genes are sequenced, dsRNAs constructed based on those sequences, and the phenotypic changes elicited by impaired the expression thereof evaluated. In preferred embodiments, crustacean genes are identified that promote growth, differentiation, reproduction and overall well being.

The following examples are provided to exemplify specific embodiments of the invention. However the practice of the invention is not limited or restricted in any way by them.

EXAMPLES

Materials and Methods

Animals and experimental viral infection: The bioassay system, experimental animals, White Spot Syndrome Virus (WSSV) and Taura Syndrome Virus (TSV) inocula used in these studies have been described elsewhere. Briefly, shrimp (L. vannamei) were stocked individually in 260 ml tissue-culture flasks and acclimated for a 2-3 day period, with 100% daily water exchange (artificial seawater, Marine Environment), and fed approximately half a pellet of commercial feed every day. When indicated, shrimp were kept in 10 gallon tanks (10-15 shrimp/tank) connected to a recirculation system with constant water flow and air supply. After acclimation, shrimp were treated by intramuscular injection of dsRNA and infected by intramuscular injection of 0.45 µm-filtered extracts of infected shrimp. In the case of TSV, the final dilution was 1×10−8 or 1×10−5, and in the case of WSSV, the final dilution was 4-6×10−8 (weight/volume dilutions). The dilutions of 1×10−8 (for TSV) and of 4-6×10−8 (in the case of WSSV) were chosen as doses that consistently resulted in mortalities between 60% and 90% over a large number of experiments and titration trials. Negative controls were injected with extracts of specific-pathogen free shrimp at equivalent dilutions. Injection volumes were 20 µl, unless otherwise specified. Mortality was recorded daily, and water exchange and feeding regimes were as described above.

dsRNA: ssRNA was transcribed in vitro from linearized plasmid constructs using T3 and T7 phage RNA polymerases (Promega), and the DNA template was then degraded by addition of DNase I (Promega) at a ratio of 1 U/µg of template. The transcripts were then purified by organic solvent extraction using standard methods, or by silica matrix absorption (RNeasy, Qiagen). Complementary RNA strands were mixed in the presence of 400 mM NaCl, 10 mM Tris-Cl, pH 7.4 and annealed by incubating at 75° C. for 15 min, 65° C. for 15 min, and room temperature for 15 min. The formation of dsRNA was monitored by size shift in agarose gel electrophoresis, and the concentration of dsRNA was measured spectrophotometrically. The DNA templates used for in vitro transcription were pBluescript vector (Stratagene) hosting either a 309 bp portion of the immunoglobulin . υ chain of the duck, Anas platyrhynchos (accession #AJ312200); a 1316 bp genomic non-coding region of clone BAC6 from the catfish Ictalurus punctatus IgH locus (accession #CC936713); a 1079 bp portion of pig Sus scrofa IgG cDNA (accession #U03778); or a 1184 bp fragment of the bacterial artificial chromosome (BAC) cloning vector pBeloBAC11. Poly C·G, poly I·C, and poly C are commercial dsRNA and ssRNA analogs (Sigma-Aldrich).

Histology and Immunohistochemistry: Whole shrimp were fixed in Davidson's solution (33% ethanol, 22% formalin, 11.5% acetic acid) for 24 hours, then transferred to 70% ethanol and stored until histological analysis by hematoxylin/eosin staining (33) and immunohistochemistry using an anti-WSSV monoclonal antibody detection system (Diagxotics).

dsRNA Sequences

1) Tested in non-specific dsRNA immune induction.

```
Duck υ:
                                         (SEQ ID NO: 1)
CTGGCAGGGCGGCGTGTCCTACGCCTGCATGGTGGTCCACGAAGGGTTGC
CCATGAGGTTCACCCAACGGCCTCTCCAGAAGACCCCCGAGCTGGACATC
TCCACCGCCCTCTGCCCGGACGCCGGCGACCAAGAACTGGACGGGCTCTG
GGCCACCATCGCCGTCTTCATCACCCTCTTCCTCCTCAGCGTCTGCTACA
GCGCCACCGTCACCTTCTTCAAGGTCAAGTGGCTTTTCTCCACCGTCCTG
CAGCTGAAGAGCGCCGGCGGCCCCTACCGCAACGTCCTGAAGGAGGCGGC
GTGAGCGGC Catfish genomic DNA:
                                         (SEQ ID NO: 2)
CTTTCTAGGGCTAGATATTGCAAACAATTTGGCAGTTTTATTCCTATATA
TATGGTTTCGATGGAAAATTCGATCCAATATCGATTCGTTATCAATATTT
CATTTAAAATGTTAGTTTTGCAGGCACAGATTCCATGTTTTAATATAAAT
GCTGGTAACTGAAACCCTCCTGCTTGGCTACATTACTGAAATACACATTT
ACGTTACCAATAAGACCTGCACAATTATGTTTCATTACTTTTTACTTTTA
CTTTGAGTAACATTGTAAAAGGAAATCATAAATATGTGCATACAGTGCAC
ACAAGGTAAGCACAAATGGCACGTAATTGTAAAAAAACAAACAAAAAAAC
AAAACATTTGTAAAAGTGCAACAGTGAAATTCATTAACAATTTGAAACGT
GTTTAAGAAATAAAACCATTTTCAAAATTCAGAACGTGAAAGAATCTGGA
GATTATCTGTAGTGCTCCTCGTCCTGAAGGAGCACTATAGATAATATTCA
CATCCTCTCAAGTAAATCACACGCATTAAGAATCGATTTAGGGATTTCCC
AAATCCATATCATTTTGTTAAATTGCTGATCGAATAAAACGGAGAATTGC
TATTTTTTACCCAGCCCTAGTGCTTTTACACCTGGTTGTCAGTCCACCCA
GTCTGAATATGAGCAAAATTGGTACTTTTGCTTCATTTGCTATTTGGTTT
GTTTTTTCATCCACACTGCACATAGTTAATTGAGCAACAAAAAGTTGTCA
GGGCTTGTACGTTCATCAGTCTGAATTATCCTCAATGAAAAAAATTATAA
GCAAACTTTATGCATATAAAATCTCAAAGATTACTTGAGCACAGAGAGCA
TGGAACCGGCTAGAAGAATTAGGTAGTCTGTATAAACAACTTTTTCTTT
TGCGTGCCACATCCAGCTTTAATTTTCTCTTTTTGTTTGTCGGACCAAAT
ATTTAGAACATGTGGCATTTCTGTTGCGCTACAGTGGTAGTTCAGTGGTT
AAGAAGTTAGACTACTGATCAGAAGCTTGTGAGTTCAAGTCCTAATACTG
CTAACCTTCCACTCTTCAGGCCTTGAGTAAGGCCCTTAACCCTCAACTGC
TTTTTAAATTTTTTTTTTTTTTACTTTATTAAAATATTAGAGTCCATAT
AAGTACATTTTTAAAGGCAAATCAATTGTATACTGTAGTAAATTGTGTGC
TGTGGTTCACATTTTGGCCTTGACCATGATTTAATTTTTTGTTGATGGAG
CTGGGTGGACAGTGCACACTCAGCTCAAAACATCCAAGCCCAACTATATC
ACCCAAAACCATGTGG Bacterial vector sequence:
                                         (SEQ ID NO: 3)
CGACGGCGACTCCCATCGGCAATTTCTATGACACCAGATACTCTTCGACC
GAACGCCGGTGTCTGTTGACCAGTCAGTAGAAAAGAAGGGATGAGATCAT
CCAGTGCGTCCTCAGTAAGCAGCTCCTGGTCACGTTCATTACCTGACCAT
ACCCGAGAGGTCTTCTCAACACTATCACCCCGGAGCACTTCAAGAGTAAA
CTTCACATCCCGACCACATACAGGCAAAGTAATGGCATTACCGCGAGCCA
```

-continued
TTACTCCTACGCGCGCAATTAACGAATCCACCATCGGGGCAGCTGGTGTC
GATAACGAAGTATCTTCAACCGGTTGAGTATTGAGCGTATGTTTTGGAAT
AACAGGCGCACGCTTCATTATCTAATCTCCCAGCGTGGTTTAATCAGACG
ATCGAAAATTTCATTGCAGACAGGTTCCCAAATAGAAAGAGCATTTCTCC
AGGCACCAGTTGAAGAGCGTTGATCAATGGCCTGTTCAAAAACAGTTCTC
ATCCGGATCTGACCTTTACCAACTTCATCCGTTTCACGTACAACATTTTT
TAGAACCATGCTTCCCCAGGCATCCCGAATTTGCTCCTCCATCCACGGGG
ACTGAGAGCCATTACTATTGCTGTATTTGGTAAGCAAAATACGTACATCA
GGCTCGAACCCTTTAAGATCAACGTTCTTGAGCAGATCACGAAGCATATC
GAAAAACTGCAGTGCGGAGGTGTAGTCAAACAACTCAGCAGGCGTGGGAA
CAATCAGCACATCAGCAGCACATACGACATTAATCGTGCCGATACCCAGG
TTAGGCGCGCTGTCAATAACTATGACATCATAGTCATGAGCAACAGTTTC
AATGGCCAGTCGGAGCATCAGGTGTGGATCGGTGGGCAGTTTACCTTCAT
CAAATTTGCCCATTAACTCAGTTTCAATACGGTGCAGAGCCAGACAGGAA
GGAATAATGTCAAGCCCCGGCCAGCAAGTGGGCTTTATTGCATAAGTGAC
ATCGTCCTTTTCCCCAAGATAGAAAGGCAGGAGAGTGTCTTCTGCATGAA
TATGAAGATCTGGTACCCATCCGTGATACATTGAGGCTGTTCCCTGGGGG
TCGTTACCTTCCACGAGCAAAACACGTAGCCCCTTCAGAGCCAGATCCTG
AGCAAGATGAACAGAAACTGAGGTTTTGTAAAC Pig IgG:
(SEQ ID NO: 4)
GCCCCCAAGACGGCCCCATCGGTCTACCCTCTGGCCCCTGCGGCAGGGA
CGTGTCTGGCCCTAACGTGGCCTTGGGCTGCCTGGCCTCAAGCTACTTCC
CCGAGCCAGTGACCGTGACCTGGAACTCGGGCGCCCTGACCAGTGGCGTG
CACACCTTCCCATCCGTCCTGCAGCCGTCAGGGCTCTACTCCCTCAGCAG
CATGGTGACCGTGCCGGCCAGCAGCCTGTCCAGCAAGAGCTACACCTGCA
ATGTCAACCACCCGGCCACCACCACCAAGGTGGACAAGCGTGTTGGAATA
CACCAGCCGCAAACATGTCCCATATGCCCAGGCTGTGAAGTGGCCGGGCC
CTCGGTCTTCATCTTCCCTCCAAAACCCAAGGACACCCTCATGATCTCCC
AGACCCCCGAGGTCACGTGCGTGGTGGTGGACGTCAGCAAGGAGCACGCC
GAGGTCCAGTTCTCCTGGTACGTGGACGGCGTAGAGGTGCACAGGCCGA
GACGAGACCAAAGGAGGAGCAGTTCAACAGCACCTACCGTGTGGTCAGCG
TCCTGCCCATCCAGCACCAGGACTGGCTGAAGGGGAAGGAGTTCAAGTGC
AAGGTCAACAACGTAGACCTCCCAGCCCCCATCACGAGGACCATCTCCAA
GGCTATAGGGCAGAGCCGGGAGCCGCAGGTGTACACCCTGCCCCCACCCG
CCGAGGAGCTGTCCAGGAGCAAAGTCACGCTAACCTGCCTGGTCATTGGC
TTCTACCCACCTGACATCCATGTTGAGTGGAAGAGCAACGGACAGCCGGA
GCCAGAGAACACATACCGCACCACCCCGCCCCAGCAGGACGTGGACGGGA
CCTTCTTCCTGTACAGCAAACTCGCGGTGGACAAGGCAAGATGGGACCAT
GGAGACAAATTTGAGTGTGCGGTGATGCACGAGGCTCTGCACAACCACTA
CACCCAGAAGTCCATCTCCAAGACTCAGGGTAAATGAGCCACCCGCTGCA
CCCCACGTGCTCTCGGGTCCCGCGAGCTCGCCTGAGCCCCAGCGCTGTGT
ACATACGTCCCGGGCCAGCATGAAATAAA 2) Tested in anti-WSSV sequence-specific RNAi protection.

RR (small subunit of
ribonucleotide reductase of WSSV):
(SEQ ID NO: 5)
ACATTTCCCAGAGATCTTCATGGACAATGGAGCGGGATACAAAACGGTT
GGGGTTTTCTCTTGTAAGTAAGTGTTTAGACGTATCTACTTGCATAATG
AGTTTTTTGGTGAATTTGTCAAACACTTCCTGGGCAATCCTCTTTTTCT
CCTCGGTTTTATATTCTGACTTGATTTCTTCAGCCACTTGGTTGGCTTG
CTCCATATTCAGACCAGTAACGGTGAACAGTTTGATTGACTCCATTTCT
GGGGTTGTTGGTATTATTGGAGTAATAATGGAAGTTGACGGTAGGACCG
ATGACAGGGGAATGATGCTGTGGTGTGAGAAGTGGCCATATTTATACTC
ATGCGGCTGAGTCTGGAGGGGGGGTTGCCATCAATCAGCCTTTTTAGT
CGGTATCGGAATCAGTGTGGCCAATTCACAAACCATCTCTGCTCTTTAT
TTTGCAGACGGTCTCAAATACACCCTTCTGGTCTTGCAAGATCTCCTCA
ATAACTGGTCGATGTCTTCAATTTTTATGTAGGAAGTCTTTCATGGAAG
ATATTTNCTGGTTGTTCACAAANGCCCACAGTTCCTTATATCTGGT vp2B (envelope protein of WSSV):
(SEQ ID NO: 6)
ATGGATCTTTCTTTCACTCTTTCGGTCGTGTCGGCCATCCTCGCCATCA
CTGCTGTGATTGCTGTATTTATTGTGATTTTTAGGTATCACAACACTGT
GACCAAGACCATCGAAACCCACACAGACAATATCGAGACAAACATGGAT
GAAAACCTCCGCATTCCTGTGACTGCTGAGGTTGGATCAGGCTACTTCA
AGATGACTGATGTGTCCTTTGACAGCGACACCTTGGGCAAAATCAAGAT
CCGCAATGGAAAGTCTGATGCACAGATGAAGGAAGAAGATGCGGATCTT
GTCATCACTCCCGTGGAGGGCCGAGCACTCGAAGTGACTGTGGGGCAGA
ATCTCACCTTTGAGGGAACATTCAAGGTGTGGAACAACACATCAAGAAA
GATCAACATCACTGGTATGCAGATGGTGCCAAAGATTAACCCATCAAAG
GCCTTTGTCGGTAGCTCCAACACCTCCTCCTTCACCCCCGTCTCTATTG
ATGAGGATGAAGTTGGCACCTTTGTGTGTGGTACCACCTTTGGCGCACC
AATTGCAGCTACCGCCGGTGGAAATCTTTTCGACATGTACGTGCACGTC
ACCTACTCTGGCACTGAGACCGAGTAA

Example 1

Use of dsRNA-Mediated Genetic Interference to Block Viral Infection in the Marine Shrimp *Litopenaeus vannamei*

In this example, it is shown that treatment of shrimp with dsRNA representing genes encoded in the WSSV genome effectively protected them against WSSV infection. These results provide the first evidence of an RNAi pathway in shrimp, and open the possibility of developing antiviral strategies using dsRNA-related therapeutics in aquaculture.

Shrimp and WSSV: The bioassay system, experimental animals, and WSSV inoculum used in these studies have been described elsewhere. Briefly, Litopenaeus vannamei (1-2 g) were stocked individually in 260 ml tissue-culture flasks and acclimated for a 3 day period, with 100% daily water exchange (artificial seawater, Marine Environment®, and fed a small piece (about half a pellet) of commercial feed every day. Animals were then treated by intramuscular injection of dsRNA and infected with WSSV either by injection or per os, as indicated. Mortality was recorded daily, and water exchange and feeding regimes performed as described above.

WSSV and shrimp EST's and preparation of dsRNA: A *L. vannamei* EST collection (http://www.marinegenomics.org,]) that includes suppression subtractive hybridization libraries (PCR Select, Clontech) prepared from WSSV challenge experiments was used as a source of WSSV and shrimp expressed genes. All ESTs used in this study have been deposited in the National Center for Biotechnology Information (NCBI) databases. ESTs encoding portions of shrimp signal transducer and activator of transcription (STAT), and I-kappB kinase catalytic subunit (IKBK), have accession numbers CA991435, and CA9914534. The sequences of the ESTs representing portions of hemocyanin and PJV627-like are available at www.marinegenomics.org (*L. vannamei* ID numbers 1405 and 1263, respectively). PJV627 is an EST of unknown function from *Marsupenaeus japonicus* [Rojtinnakorn, 2002 #430]. ESTs for WSSV genes vp28, small subunit of ribonucleotide reductase, and DNA polymerase can also be found at www.marinegenomics.org (*L. vannamei* ID numbers 6321, 6390, and 5789, respectively). Total or partial EST inserts were sub-cloned into pBluescript (Strategene), PGEM-TEZ (Promega), or pCR4-TOPO (Invitrogen) for bi-directional in vitro transcription using SP6 or T3 and T7 phage promoters, under standard conditions. Single stranded RNA transcripts were extracted with organic solvents and ethanol-precipitated using standard methods. Complementary stands were annealed at 75° C. for 15 min, 65° C. for 15 min, and room temperature for 15 min, in 10 mM Tris-Cl, 400 mM NaCl, pH 7.5. The formation of dsRNA was monitored by size shift in agarose gel electrophoresis, and concentration of dsRNA was measured spectrophotometrically. The segment of the IKBK EST used to synthesize dsRNA corresponds to position 15 to 390 in CA991434, and the segment of the STAT EST used to make STAT dsRNA corresponds to positions 14-383 in CA991435. The full-length ESTs were used to produce hemocyanin, PJV627-like, and all of the WSSV genes dsRNAs. As a control for the sequence-independent antiviral effects of dsRNA, a construct encoding 309 bp from the immunoglobulin υ of the duck Anas platyrynchos (accession # AJ312200) was used.

Expression analysis: Animals were sacrificed and dissected, tissues were preserved in RNA later (Ambion) and stored at −20° C. until used. Total RNA was isolated using RNeasy kits (Qiagen). For northern analysis RNA was resolved by formaldehyde-agarose electrophoresis, transferred to nylon, and probed with 32P-labelled DNA as described. Membranes were washed using standard procedures, and data obtained by autoradiography. Probes were prepared from full length EST inserts. For RT-PCR, single stranded cDNA was prepared using Powerscript RT (Clontech) and primed with oligodT, the RT reaction was then diluted 2-fold, and 1 µl used as template for PCR using gene-specific primers. PCR conditions were 94° C. for 2 min, (94° C. for 30 sec, 65° C. for 30 sec, 72° C. for 1 min) 26 cycles, 72° C. for 2 min. STAT mRNA was detected using the following primers: forward CTG TCT GAG CGA AAC TTC ACA (SEQ ID NO: 7) and reverse AAG TCA GCG ATC ACA TCA GCT (SEQ ID NO: 8). IKBK mRNA was detected using the following primers: forward CCA GCA ACT AGA AGG CTC ACT (SEQ ID NO: 9) and reverse CGG TTC TTG CTG CAT CTT GCA (SEQ ID NO: 10). Ribosomal protein S3A mRNA was detected using the following primers: forward CCA GAA TGA GAC TGA TGC TGA (SEQ ID NO: 11) and reverse CAC GGG TGA TAA TGT CTA CCA (SEQ ID NO: 12).

Results dsRNA triggers specific depletion of cognate cellular mRNA in shrimp: Based on the wide conservation of the RNAi pathway, we hypothesized that mechanisms similar to RNAi are present in *L. vannamei*. To test this, we injected dsRNA for portions of shrimp genes and analyzed the relative levels of the targeted mRNAs by Northern Blot analysis and RT-PCR. FIG. 1a shows that injection of hemocyanin dsRNA dramatically reduces the level of hemocyanin mRNA in hepatopancreas. This mRNA depletion is sequence-specific, since injection of dsRNA encoding an unrelated gene (PJV627-like) has no effect on hemocyanin expression, and hemocyanin dsRNA-injected shrimp express normal levels of this unrelated mRNA (FIG. 1a). It is also apparent that targeting this gene of unknown function with dsRNA results in no detectable depletion of the corresponding mRNA. Low molecular weight hybridization signals related to this ineffectively targeted mRNA can be observed, suggesting intermediate degradation products resulting from activation of a putative RNAi mechanism. Similar intermediates have been observed in *Drosophila* cells upon induction of RNAi [9]. It seems reasonable that the efficiency of dsRNA-induced mRNA depletion is gene-specific, and likely influenced by distinct mechanisms of transcriptional and translational regulation, sub-cellular compartmentalization, and other characteristics that are specific to each mRNA.

We have further confirmed that down-regulation of specific mRNA expression is achievable for other genes and in other tissues in the shrimp system (FIG. 1, b and c). We injected dsRNA representing portions of signal transducer and activator of transcription (STAT) and IkappaB kinase catalytic subunit (IKBK) cDNAs of shrimp. RT-PCR shows that the corresponding mRNAs are depleted from gills of dsRNA-treated animals, when compared to saline-injected animals. The sequence-specificity of this down-regulation is revealed by the unaffected expression of a ribosomal protein mRNA in all animals (FIG. 1, b, and c), and by the normal expression of IKBK mRNA in STAT dsRNA-treated animals, and vice-versa (data not shown). mRNA depletion induced by cognate dsRNA was not complete however, and traces of both STAT and IKBK mRNAs are still detectable by RT-PCR after dsRNA treatment. There is also some individual variability observed in both the levels of expression and the efficiency of mRNA depletion induced by dsRNA.

We have further confirmed that down-regulation of specific mRNA expression is achievable for other genes and in other tissues in the shrimp system (FIGS. 1A-B). We injected dsRNA representing portions of signal transducer and activator of transcription (STAT) and IkappaB kinase catalytic subunit (IKBK) cDNAs of shrimp. RT-PCR shows that the corresponding mRNAs are depleted from gills of dsRNA-treated animals, when compared to saline-injected animals. The sequence-specificity of this down-regulation is revealed by the unaffected expression of a ribosomal protein mRNA in all animals (FIGS. 1A-B), and by the normal expression of IKBK-mRNA in STAT dsRNA-treated animals, and vice-versa (data not shown). mRNA depletion induced by cognate dsRNA was not complete however, and traces of both STAT and IKBK mRNAs are still detectable by RT-PCR after dsRNA treatment. There is also some individual variability observed in both the levels of expression and the efficiency of mRNA depletion induced by dsRNA.

Example 2

Further Characterization of Anti-WSSV Protection by dsRNA Encoding Four WSSV Genes Task 1 aims to provide an initial comparison of selected WSSV genes. Based upon the quality of the EST clones and the expected role of the gene in viral replication, differences in efficacy of dsRNA in generating a protective effect may be found. These experiments will establish methods for dsRNA production and allow evaluation of some of the most important clones from our WSSV EST collection.

Clone 4 WSSV Genes (vp26, vp19, Thymidylate Kinase, DNA Polymerase) and Produce Long dsRNA Methods Six WSSV genes rather than 4 were used. These were vp19 (an envelope protein, GenBank accession#AAO69661); vp26 (a protein of the nucleocapsid, GenBank accession#AAO69663); vp28 (an envelope protein, GenBank accession#AAL33423); VF (a viral protein of unknown function, GenBank accession#AAL33255), DNA polymerase (an enzyme involved in the replication of the viral genome, GenBank accession#NP_478036), and ZF (a putative zinc-finger transcription factor, accession#NP_477987). These genes were selected as potential targets based on their known or surmised function; two (vp19 and vp28) are envelope proteins that have been suggested to play a role in viral infection of host cells and to be a target for vaccine production (Witteveldt J, Vlak J M, Van Hulten M C. Protection of *Penaeus monodon* against white spot syndrome virus using a WSSV subunit vaccine. (Fish Shellfish Immunol. 2004 May;16(5): 571-9)); the vp26 protein is known to be a component of the nucleocapsid; DNA polymerase should be required for viral genome replication; and ZF has a putative role in controlling the expression of the WSSV genome. Thus, these genes represent at least 4 distinct functions in WSSV and therefore present a range of targets for protection against infection by RNAi-mediated downregulation. The genes were amplified by PCR from our EST collection and subdloned into vectors with opposing phage promoters (pCR4 from Invitrogen, in which the insert of interest is flanked by T7 and T3 promoters). Plasmid DNA was purified, linearized and used for in vitro transcription of the RNA. The RNA was purified, annealed, quality checked by gel electrophoresis, and quantified. A modified RNA synthesis protocol was followed, that allows the up-scaling of synthesis reactions for production of milligram amounts of RNA.

Results and Discussion

The genes identified above except for vp19 and thymidylate kinase successfully amplified from the EST collection and cloned in the vector of interest. The gene encoding vp19 was cloned by PCR amplification from WSSV-infected shrimp tissue. The identity of all the genes cloned was verified by sequencing, and the functionality of the recombinant constructs was checked by in vitro transcription. The single-stranded RNA and the annealed dsRNA product were assayed by agarose gel electrophoresis as seen in FIG. 3. Typical in vitro transcription reactions yield approximately 25 ug dsRNA per lug DNA template.

Conclusions:
1. Methods for the cloning and in vitro transcription of viral genes have been applied and standardized.
2. Utilizing the techniques applied here it should be possible to produce dsRNA from selected genes of interest for yan shrimp virus for which EST clones or sequence information is available.

Example 3 dsRNA Preparations Alone and In Combination for Protection Against WSSV Infection Methods Five of the genes of the prior example were tested for their ability to protect shrimp from infection with WSSV. The experiment that was performed was as follows: 1) the challenge dose of virus was given by feeding WSSV-infected shrimp tissue (5% of body weight daily) for 2 days. The control (uninfected) animals were fed the same amount of uninfected shrimp tissue (5% daily) for 2 days. This per os challenge with a lethal dose of virus was chosen over injection of an $LD_{90}$ dose of WSSV because it is more representative of the mode of viral challenge in a real world environment and because it provides much more stringent testing of the shrimp's resistance. The protective effect of the WSSV genes was not compared to that of non-specific-dsRNA (e.g. duck IgY). Comparing the results obtained in this study using non-specific stimulation, with our initial results using virus-specific sequences, it was quite clear that several-fold greater protection could be achieved using dsRNA of a WSSV gene. In addition, a comparison of the protective effects of specific (vp19) and non-specific (polyC:G) dsRNAs is included in the experiments shown in the table in Example 5 and FIG. 9. The injection of dsRNA (12 µg) was given intramuscularly 4-6 hours before the per os challenge was initiated. Statistical analysis was conducted using a one way ANOVA using the Kruskal-Wallis method.

In all the trials, the animals were challenged in a recirculating system composed of 25 tanks. Each tank drains into a collective sump and the water is filtered to 5 µm before it is passed through a biological filter. The water is filtered to him and treated with a 40 W UV sterilizer ($9 \times 10^5$ W/cm²s) before it returns to each tank. The animals were fed 1 to 2 commercial feed pellets per day. The filters were changed regularly. The salinity was maintained at 30 ppt and the temperature at 27° C. There was a 48 hour acclimation period prior to all viral challenges. Mortality was monitored and dead animals were removed daily. There were 10 animals (1-3 g) per tank and three tanks per treatment.

Results and Discussion

The efficacy of the 5 chosen WSSV genes in the protection experiments varied (FIG. 4): the ZF and vp19 genes gave good protection (better than uninfected animals: 80-86% survival) whereas the other three genes (vp26, vp28 and VF) gave lesser protection (between 40 and 52%). A mixture of the dsRNA of all 5 genes was tested, and found to give intermediate protection, of 70% survival at 10 days. All genes and the mixture of dsRNA were significantly different from the positive control except for VF (P=0.072). The vp19, ZF and the MIX (P<0.001) produced slightly more significant survival than the negative control (P=0.003) when compared to the WSSV positive treatment. The mortalities in the negative group were unexpected but were not due to accidental WSSV infection, as tested by PCR. The mortality in the negative group did not affect the interpretation or significance of the results. The most protective genes, vp 19 and ZF were significantly different than the least protective gene VF (P=0.011 and 0.016 respectively).

Conclusions:
1. Administration by intramuscular injection of 12 µg of dsRNA encoding vp19 and ZF gave essentially complete protection against a lethal per os viral challenge. The other 3 genes tested were protective but with lower efficacy.
2. A mixture of the 5 dsRNAs gave protection that was in the middle of the range for the 5 genes when given individually.

Example 4 dsRNA Induces General Antiviral Immunity in a Marine Invertebrate (Shrimp)

We first observed that injection of shrimp with dsRNA afforded antiviral protection while testing the effects of RNAi-mediated down-regulation of signal transduction pathways on the outcome of challenge with Taura Syndrome Virus (TSV). Our experimental approach was to inject purified cognate dsRNA and then challenge animals with TSV to explore whether animals in which genes of interest were down-regulated would display increased susceptibility to virus. Surprisingly, injection of any dsRNA, whether representing shrimp genes or non-specific dsRNA controls, resulted in increased survival to TSV challenge (not shown). This initial observation prompted us to address the possibility that, as in vertebrates, dsRNA can induce an antiviral program in shrimp.

To explore whether dsRNA induces a general antiviral response in the shrimp, we analyzed the effect of dsRNA treatment on infection with TSV, a single stranded RNA virus (Bonami et al., J. Gen. Virol. 78 (Pt0.2):313-319 (1997)), and on infection with WSSV, a complex enveloped double stranded DNA virus (Mang et al., J. Virol. 75:11811-20 (2001)). Reductions in cumulative mortality of 50 to 75% were observed in animals treated with dsRNA, compared with mock-treated animals (FIGS. 5A-B). The level of antiviral protection was reduced (to about 12%) when shrimp were subjected to a significantly higher dose of TSV (FIG. 5a), suggesting that, like any immune response, dsRNA-induced antiviral protection in shrimp can be overwhelmed by increasing the load of infectious agent. The dsRNA used to protect against both TSV and WSSV in the experiments described herein was transcribed from the gene for the duck immunoglobulin γ heavy chain. This sequence has no similarity to any known shrimp gene, or to the genomes of WSSV (accession #NC_003225) or TSV (accession #NC-003005). Thus, the observed antiviral response induced by duck dsRNA is unlikely to involve the sequence specific RNAi pathway, and therefore may represent a more general antiviral mechanism active against two unrelated viruses.

The challenge system used in the experiments, including culture medium and rearing conditions, were highly standardized notwithstanding, the absolute values corresponding to cumulative mortality are not entirely consistent. It is believed that the variability may be attributable to batch-to-batch differences in shrimp used. As the experiments require relatively young shrimp (1-3 g average weight) it is unfeasible to use shrimp from a single batch over a prolonged time period.

Preliminary experiments (data not shown) suggested that 1 µg of duck dsRNA was close to the minimal effective dose required to induce protection against WSSV infection, and that as much as 100 µg of dsRNA could be injected into a shrimp of 1-2 g, without causing obvious signs of toxicity. Thus, intermediate doses of 7-15 µg were subsequently used in the studies reported here to investigate the characteristics of the dsRNA-induced antiviral response in shrimp.

Effect of dsRNA dose on antiviral protection: The following table summarizes an experiment in which different doses of duck υ dsRNA were injected prior to infection with WSSV. Final Cumulative Percent Mortality (CPM) values are shown.

| dsRNA (µg/1–2 g shrimp) | CPM |
|---|---|
| 1 | 71 |
| 0.2 | 84 |
| 0.04 | 90 |
| 0.008 | 97 |
| 0.0016 | 95 |
| 0.00032 | 100 |
| 0 (positive control) | 100 |
| 0 (negative control) | 0 |

In an independent experiment, higher dsRNA doses were titrated to determine if more than 1 µg of dsRNA would have an effect (either positive or negative) on survival upon WSSV challenge. The cumulative percent mortality values obtained are summarized in the following table:

| dsRNA (µg/1–2 g shrimp) | CPM |
|---|---|
| 14 | 8 |
| 5 | 10 |
| 1.6 | 5 |
| 0 (positive control) | 63 |
| 0 (negative control) | 3 |

The absolute CPM values varied somewhat in these two assays, for both positive controls and protected groups, even though the experimental conditions were kept the same. The protective effects of dsRNA were, however, consistent. Taken together, these dose-response profiles suggest that around 1 µg of dsRNA (for duck □) consistently protects shrimp of 1-2 g against sub-LD100 infection with WSSV. They also suggest that 1 µg may be close to a threshold of protection, and thus we decided to use 7-15 µg in further experiments, since we have injected as much as 100 µg of dsRNA in shrimp without any signs of toxicity.

Confirmation that the induction of an antiviral state by dsRNA was sequence-independent was sought by challenging shrimp with WSSV after treatment with four different types of unrelated dsRNA sequences. We used sequences derived from vertebrate immunoglobulin genes (duck and pig), fish non-coding genomic DNA, and bacterial vector sequence (pBeloBAC 11 vector). Each one of these sequences induced protection against WSSV infection (FIG. 5b). To determine whether dsRNA treatment inhibits viral infection or results in attenuation of WSSV induced mortality without affecting viral accumulation in the host, histological analysis was performed on shrimp challenged with WSSV with or without pre-treatment with dsRNA. Dramatic differences were observed when we tested the accumulation of WSSV particles and the occurrence of classical tissue damage in control and dsRNA-treated shrimp 36 and 72 hours after infection (data not shown, and FIGS. 5C-E). Histological section of control infected animals revealed large basophilic granular viral inclusions in nuclei of gastric and cuticular epithelial tissues (not shown), as well as hemopoieitc tissues (FIG. 5D.) These features were absent from animals protected by dsRNA-treatment (FIG. 5E). These observations suggest that WSSV fails to accumulate significantly in dsRNA-treated shrimp, probably due to the induction of antviral protection system. Collectively, these data support the conclusion that dsRNA induces, in a sequence independent manner, an antiviral response in shrimp.

Minimum Protective Dose

Methods

To test the effect of dose of dsRNA on the protection afforded against WSSV challenge, the following experimental design was adopted. The two species of dsRNA that gave the greatest and least protection, vp19 and VF, respectively, were chosen for test at "full-strength" (10 µg), and at 10-fold lower dilutions (1 and 0.1 µg). The dsRNA was administered intramuscularly 4-6 hours before per os challenge with WSSV infected tissue, and survival was measured over a 10-day period. The Kruskal-Wallis method was used to determine statistical significance.

Results and Discussion

The results (FIG. 6) confirmed that vp19 was a better protector against viral challenge, and also showed that the protective effect could be diluted out for both genes. While the 1 µg dose of vp19 gave protection almost as good as for the 10 µg dose (80% versus 90%), at 0.1 µg the protection had dropped to 36%. All of the vp19 doses (10, 1 and 0.1 µg) were statistically different from the positive control (P<0.001, <0.001, and 0.023 respectively). The 0.1 µg dose was significantly less protective then the other two doses. (P=0.002). In the case of the VF dsRNA, protection at the 3 dose levels was 72%, 46% and 38%. All of these doses (10, 1 & 0.1 µg), were also significantly different from the positive control (P<0.001, 0.013, & 0.0.16). Statistical analyses showed that the highest dose of VF was similar to higher doses of vp19 (10 µg P=0.009 and 1 µg P=0.010) and lower VF doses were grouped with the lowest vp19 dose (P=0.002 to 0.003).

Conclusions

1. The greater protective effect of vp19 compared to VF at doses of 10 and 1 µg was confirmed.
2. The effectiveness of the dsRNA protections was titrated out with dilution, and for both vp19 and VF was around 36-38% at the 0.1 µg dose.

Figure 7B:
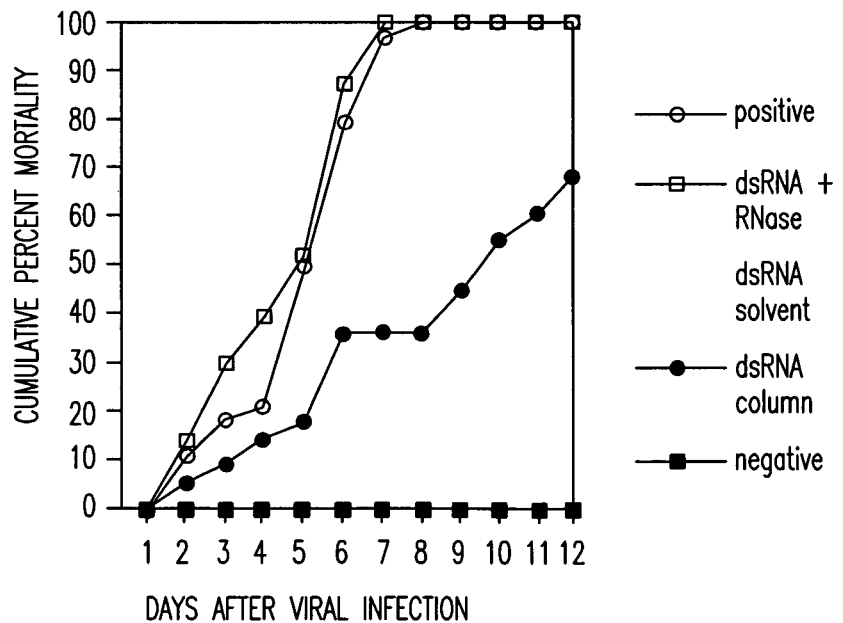

Induction of the antiviral state is due to RNA: Some potent inducers of innate immunity can exert strong effects on sensitive cells at relatively low concentrations. We considered the possibility that the relative resistance of dsRNA-treated animals to viral challenge was due to contaminants in the dsRNA preparations that could co-purify with dsRNA during organic solvent extraction (e.g. LPS, DNA). Additionally, we considered the possibility that compounds present in the RNA preparations could directly inactivate the viruses used in our studies, even when 72 hours were allowed to pass between dsRNA treatment and viral injections. To address these issues, we conducted a series of experiments in which we subjected the animals to a two-step dsRNA application regime: first, we injected animals with dsRNA 72 hours before viral challenge as done before, and then applied an additional dose of dsRNA mixed with the viral preparation. We reasoned that, if contaminants in dsRNA preparations were responsible for direct inactivation of the virus, we would observe high survival rates in shrimp injected with viral inoculum that has been mixed with the dsRNA preparations. FIG. 7 shows that a single dsRNA dose 72 hours before viral challenge protects shrimp against WSSV to a similar extent as two applications of dsRNA (72 hours before infection and injection, of virus/dsRNA mixtures). Furthermore, when dsRNA was injected only as a mixture with the viral inoculum, poor protection (less than 10% reduction in mortality) was observed relative to the 72 hour pretreatment or the double treatment with dsRNA. These results demonstrate that direct inactivation of the virus by dsRNA or by putative contaminants cannot account for the observed antiviral protection. Furthermore, FIG. 7b shows that RNase treatment destroyed the antiviral protection afforded by our preparations, and that dsRNA purified from in vitro transcription reactions by two different methods (organic solvent extraction or silica matrix adsorption) have similar abilities to induce the antiviral response. Taken together, these results demonstrate that intact RNA (and not other compounds present in the dsRNA preparations) is the inducer of the observed antiviral immunity in shrimp.

Poly C-G, but not poly I-C or poly C induces the antiviral state: Poly I-C is a potent inducer of the innate antiviral response in vertebrates, and a popular experimental tool for studying the biology of dsRNA in these systems. We explored the possibility that this and other synthetic commercial RNAs would also induce the antiviral response in shrimp. FIG. 8 shows that poly I·C failed to induce protection against WSSV infection, while another dsRNA analogue, poly C·G was a highly effective inducer of antiviral protection. This result suggests differences in the mechanisms for recognition of dsRNA between vertebrates and shrimp, and further supports the notion that dsRNA can induce the antiviral response in shrimp independently of the method by which it is prepared or purified. Importantly, the synthetic ssRNA poly C failed to induce antiviral protection, suggesting that, like its vertebrate counterpart, the antiviral system of the shrimp is capable of discriminating between ssRNA and dsRNA.

The precise molecular nature of the antiviral response induced by dsRNA in shrimp remains to be elucidated. The characterization of the molecular mechanisms of recognition and response to dsRNA in invertebrate species will provide insight into the evolution of innate antiviral immunity. It is hypothesized that a dsRNA-induced systemic antiviral response will be present in other invertebrates. The widespread existence of this response in other invertebrates will have important implications for the use of RNAi for reverse genetic analysis in invertebrates.

Example 5

Adjuvant Effect of Non-Specific dsRNA on Protection Elicited by a Specific (WSSV) dsRNA Methods The cost and complexity of preparation of gene specific dsRNA could be an important impediment to commercialization. As such, an experiment was designed to determine if the addition of non-specific dsRNA (polyC:G) could compensate for the loss of activity of the specific WSSV dsRNA seen upon dilution. Accordingly, dsRNA for vp19 in amounts varying between 0.012 and 1 ug was mixed with polyC:G to maintain a constant dose of 1 µg, as shown in Table 1. Shrimp were injected with the vp19/polyC:G mixture 4-6 hours before per os challenge was initiated, and the survival monitored over 10 days. Statistical analysis was done with a one way ANOVA using the Kruskal-Wallis method.

TABLE 1

| Treatment | vp19 dsRNA (µg/animal) | Poly CG (µg/animal) |
|---|---|---|
| POSITIVE | 0 | 0 |
| NEGATIVE | 0 | 0 |
| 1000 | 1.000 | 0 |
| 333 | 0.333 | 0.667 |
| 111 | 0.111 | 0.889 |
| 37 | 0.037 | 0.963 |
| 12 | 0.012 | 0.988 |
| 0 | 0 | 1.000 |

Results

As shown in FIG. 9, shrimp treated with 1 µg of vp19 dsRNA and 0.333 µg of vp19 dsRNA plus 0.667 µg of polyC:G showed essentially the same survival, of 86-92% (P=0.574). The group treated with 0.111 µg vp19 dsRNA showed 70% survival, the groups treated with 0.037 and 0.012 µg of vp19 dsRNA (and 0.963 or 0.988 µg of poly C:G respectively) showed between 20 and 30% survival, while the animals treated with 1 µg polyC:G showed a scant 6% survival. A significant drop in protection was observed when the vp19 dose was reduced from 0.111 µg to 0.037 µg (P<0.001).

Conclusions

The cumulative the results of the experimental examples suggest that the addition of polyC:G to dsRNA encoding a WSSV gene increases the proportion of shrimp surviving viral challenge by approximately 2-fold. This is of great importance in that the cost of production of viral gene specific dsRNA would be expected to be much higher than that of polyC:G. The reason for the enhanced effect is unclear but may be related to up regulation of a generalized antiviral response.

The greater potency of dsRNA encoding a WSSV gene (vp19) than that of non-specific dsRNA (polyC:G) was clearly demonstrated (significant, P<0.001).

Example 6

Construction of Yeast Expression Vectors that Inducibly Express Viral dsRNA in *Saccharomyces*

Plasmids were constructed that contain the GAL1 (galactose inducible promoter), a desired gene operably linked thereto (vp19 or ZF sequence of WSSV), two selectable markers, URA (uracil gene) and AMP (ampicillin gene), a desired gene linked to the desired dsRNA, resulting in a vector which when introduced into a *Saccharomyces*, may be selected for under selective conditions (uracil negative), and which expresses the desired gene and dsRNA when cultured under galactose inducible conditions. (See FIG. 10). As shown schematically in FIG. 11, optionally yeast experiments are further conducted to select strains having optimal levels and timing of expression, and culture parameter that optimize dsRNA yield.

As shown by the results contained in FIG. 12, *Saccharomyces* transformants express detectable levels of WSSV encoded dsRNA when transformed with an expression vector containing VP19 or ZF sequences of WSSV. In the example, 10 micrograms of total RNA were extracted from transformed yeast and analyzed by Northern Blot, using probes for vp19, ZF or yeast actin (as a positive control). These results demonstrate that WSSV-related RNA is expressed in yeast and illustrates the specificity of detection in the Northern analysis.

As further shown by the results contained in FIG. 13, yeast express double stranded RNA when transformed with vector containing ZF sequences of WSSV. In these experiments, 10 micrograms of total RNA with a ZF-expressing vector were analyzed by Northern Blot. Probes for each strand (antisense, left and sense, right) of the RNA were used, and both detected their respective targets. Thus, these results confirmed that yeast expressed both strands of the WSSV ZF sequence. Additionally, as shown in FIG. 13, the standards (to the right of each gel) allowed the approximation of the amount of WSSV ZF RNA (approximately 50 nanograms) present in each sample.

While it was hoped that yeast would express a desired dsRNA at detectable levels, this result was not reasonably anticipated, because of the significant possibility for any expressed dsRNA to be degraded by endogenous RNases. Based on these results, yeast should provide a suitable means to deliver a desired dsRNA to a crustacean, e.g., shrimp or other invertebrate.

Example 7

A Functional Genomics Approach to Signal Transduction Pathways Regulating Antiviral Immunity in Marine Shrimp

*Litopenaeus vannamei* is the most widely cultivated shrimp species in the world, and an important model for the study of crustacean immunity. More than a dozen pathogenic viruses are known to infect shrimp, providing a unique opportunity to study innate invertebrate antiviral responses, a traditionally neglected aspect of invertebrate immunity. By characterizing these virus-responsive genes, we aim to gain an understanding about the kinds of pathways involved in shrimp-virus relationship. Towards this end, we have generated and characterized Suppression Subtractive Hybridization (SSH) libraries using control and White Spot Syndrome Virus (WSSV)-infected shrimp tissues. Expression analysis of clones isolated from SSH libraries reveals that several genes with putative immune function are regulated during WSSV infection. The novelty of the molecular mechanisms governing the shrimp-WSSV system is underscored by the significant proportion of genes to which no function can be ascribed based on sequence analysis. We have generated a *L. vannemei* cDNA microarray containing 2800 shrimp unigenes to analyze the changes in gene expression associated with the antiviral response in these animals. Global analysis of gene expression utilizing this shrimp cDNA microarray, coupled with targeted silencing using RNAi, will provide insight into the molecular events governing the antiviral response as well as other phenotypic responses in crustaceans.

Conclusions

The data presented here show that dsRNA evokes, in a marine invertebrate, protection against viral infection. This provides the first evidence that an inducible, general antiviral immune response may be expressed in an invertebrate. Other studies have suggested that microbial products (e.g. LPS, β-glucans), as well as certain viral proteins, can enhance antiviral resistance in shrimp (Chang et al., Fish Shellfish Immunol. 15:297-310 (2003); Hwang et al., Deu. Comp. Immunol. 23:54552 (1999); Song et al., Dev. Biol. Stand. 900:413-21 (1997); Takahashi et al., Fish Shellfish Immunol. 10:555-8 (2000); Witteveldt et al., J. Virol. 78:2057-61 (2004)). Our results however, further advance our knowledge on antiviral immunity in crustacea in 3 ways. First, they demonstrate an antiviral immune response that is active against 2 unrelated viruses, TSV and WSSV. The working hypothesis that we propose on the basis of these results is that dsRNA induces a general antiviral response in shrimp. Second, they show that the antiviral immune system of the shrimp responds to dsRNA as a molecular pattern, regardless of its sequence and base composition (except in the case of poly I-C). Third, they suggest a possible evolutionary link (recognition of dsRNA) between innate antiviral immunity in vertebrates and invertebrates.

While much is known of the molecular basis for antibacterial and antifungal responses in invertebrates, especially in insects (reviewed in (Hetro et al., J. Infect. Dis. 187 Suppl 2:5227-334 (2003)), there is no information concerning immune mechanisms directed against virus infections in any invertebrate. It seems clear that invertebrates lack antiviral systems homologous to vertebrate interferon, based on the analysis of four complete invertebrate genomes (i.e. *Drosophila melanogaster, Anopheles gambiae, Caenorhabditis elegans*, and *Ciona intestinalis*). However, the absence of homologous genes does not rule out the existence of invertebrate immune systems analogous to those present in vertebrates. For instance, antigen-specific immune memory has recently been demonstrated for a crustacean in the context of parasitic infection (Kurtz et al., Nature, 425:37-8 (2003)). This is surprising, since a bona fide adaptive immune system homologous to the vertebrate system, which is based on T and B lymphocytes and rearranging antigen receptor genes, is clearly absent from invertebrates. Genetic diversification, and the acquisition of novel gene function during the evolution of the metazoa may have resulted in convergent evolution of antiviral immunity. Thus, focusing on function rather than sequence homology may hold the key to understanding the evolution of antiviral immunity at the molecular level.

The demonstration that dsRNA induces an antiviral program in an invertebrate opens the possibility of finding novel molecular mechanisms of innate immunity. It would be surprising if shrimp expressed genes homologous to IFNs or to IFN-induced effectors of antiviral immunity, like PKR or Mx, since these genes are lacking in the genomes of other arthropods. Interestingly, immune-responsive oligoadenylate synthetases have been identified in an invertebrate group, the sponges (Grebenjok et al., Eur. J. Biochem 269:1382-92 (2002); Kuusksalv et al., Eur. J. Biochem 232:351-7 (1995)), and the possibility that these genes exist in crustacea and play a role in antiviral immunity cannot be excluded. On the other hand, signal transduction pathways homologous to those known to regulate the vertebrate interferon response do exist in arthropods. In *Drosophila*, the JAK/STAT system regulates hemopoesis and sexual determination (reviewed in (Ziedler et al., Oncogene 19:2598-606 (2000)), and also controls expression of some immune function genes (e.g. thiol-ester containing proteins, and Turandot A) (Christophides et al., Science 298:159-65 (2002)). In *A. gambiae*, 2 homologues of STAT have been described, one of which has been shown to translocate to the nucleus in response to immune challenge (Barillas-Mury et al, EMBO. J. 18:959-6 (1999)), and our own work has identified at least one homologue of STAT in the shrimp (NCBI accession #CA991435). The discovery that mammalian TLR-3 recognizes dsRNA leading to activation of the interferon response, opens the possibility that a TLR/NF.B cassette is also involved in invertebrate antiviral immunity, and specifically in the dsRNA-induced response reported here.

The widespread existence of dsRNA-induced immune responses in other invertebrate taxa is an important issue that remains to be explored. For instance, understanding the antiviral defense mechanisms of invertebrate vectors of human disease (e.g. mosquitoes) will have important implications for public health. Furthermore, dsRNA-mediated genetic interference (RNAi) is a widely used reverse genetics tool in many invertebrate models. The possible induction of an immune response by dsRNA may need to be taken into consideration when interpreting studies using RNAi.

It is noted that the invention is not limited to the embodiments described herein and the examples presented above and that various changes and modifications may be made by those of ordinary skill in the art without departing from the scope and spirit of the appended claims.

We claim:

1. A method of producing a shrimp treated for infection by a virus that infects shrimp, comprising administering to the shrimp at least one dsRNA having sequence homology with an endogenous gene comprised in the virus that infects shrimp and further comprising administering to the shrimp at least one dsRNA that comprises a nonspecific nucleotide sequence.

2. A method of producing a shrimp treated for infection by a virus that infects shrimp, comprising administering to the shrimp at least one dsRNA that comprises a nonspecific nucleotide sequence, wherein said administration induces an antiviral response in the treated shrimp.

3. A method for inducing an antiviral response in a shrimp, comprising administering to the shrimp an effective amount of at least one dsRNA having sequence homology with an endogenous gene comprised in a virus that infects shrimp and that induces an antiviral response in the shrimp and further comprising administering to the shrimp at least one dsRNA that comprises a nonspecific nucleotide sequence.

* * * * *

SEQUENCE LISTING

<160> NUMBER OF SEQ ID NOS: 12

<210> SEQ ID NO 1
<211> LENGTH: 309
<212> TYPE: DNA
<213> ORGANISM: Anas platyrhynchos

<400> SEQUENCE: 1

```
ctggcagggc ggcgtgtcct acgcctgcat ggtggtccac gaagggttgc ccatgaggtt      60
cacccaacgg cctctccaga agaccccga gctggacatc tccaccgccc tctgcccgga     120
cgccggcgac caagaactgg acgggctctg ggccaccatc gccgtcttca tcaccctctt     180
cctcctcagc gtctgctaca gcgccaccgt caccttcttc aaggtcaagt ggcttttctc     240
caccgtcctg cagctgaaga gcgccggcgg ccctaccgc aacgtcctga aggaggcggc     300
gtgagcggc                                                            309
```

<210> SEQ ID NO 2
<211> LENGTH: 1316
<212> TYPE: DNA
<213> ORGANISM: Ictalurus punctatus

<400> SEQUENCE: 2

```
ctttctaggg ctagatattg caaacaattt ggcagtttta ttcctatata tatggtttcg      60
atggaaaatt cgatccaata tcgattcgtt atcaatattt catttaaaat gttagttttg     120
caggcacaga ttccatgttt aatataaat gctggtaact gaaaccctcc tgcttggcta     180
cattactgaa atacacattt acgttaccaa taagacctgc acaattatgt ttcattactt     240
tttactttta ctttgagtaa cattgtaaaa ggaaatcata aatatgtgca tacagtgcac     300
acaaggtaag cacaaatggc acgtaattgt aaaaaaacaa acaaaaaaac aaaacatttg     360
taaaagtgca acagtgaaat tcattaacaa tttgaaacgt gtttaagaaa taaaaccatt     420
ttcaaaattc agaacgtgaa agaatctgga gattatctgt agtgctcctc gtcctgaagg     480
agcactatag ataatattca catcctctca agtaaatcac acgcattaag aatcgattta     540
gggatttccc aaatccatat cattttgtta aattgctdat cgaataaaac ggagaattgc     600 tatttttac ccagccctag tgcttttaca cctggttgtc agtccaccca gtctgaatat     660
gagcaaaatt ggtacttttg cttcatttgc tatttggttt gttttttcat ccacactgca     720
catagttaat tgagcaacaa aaagttgtca gggcttgtac gttcatcagt ctgaattatc     780
ctcaatgaaa aaattataa gcaaacttta tgcatataaa atctcaaaga ttacttgagc     840
acagagagca tggaaccggt gctaaagaat taggtagtct gtataaacaa cttttttcttt     900 tgcgtgccac atccagcttt aatttttctct ttttgtttgt cggaccaaat atttagaaca     960
tgtggcattt ctgttgcgct acagtggtag ttcagtggtt aagaagttag actactgatc    1020
agaagcttgt gagttcaagt cctaatactg ctaaccttcc actcttcagg ccttgagtaa    1080 ggccccttaac cctcaactgc tttttaaatt tttttttttt tttactttat taaaatatta    1140
```

```
gagtccatat aagtacattt ttaaaggcaa atcaattgta tactgtagta aattgtgtgc   1200
tgtggttcac attttggcct tgaccatgat ttaattttt gttgatggag ctgggtggac    1260
agtgcacact cagctcaaaa catccaagcc caactatatc acccaaaacc atgtgg       1316
```

```
<210> SEQ ID NO 3
<211> LENGTH: 1183
<212> TYPE: DNA
<213> ORGANISM: Artificial Sequence
<220> FEATURE:
<223> OTHER INFORMATION: Description of Artificial Sequence: Synthetic
      construct of Bacterial Artificial Chromosome

<400> SEQUENCE: 3
cgacggcgac tcccatcggc aatttctatg acaccagata ctcttcgacc gaacgccggt   60
gtctgttgac cagtcagtag aaaagaaggg atgagatcat ccagtgcgtc ctcagtaagc   120
agctcctggt cacgttcatt acctgaccat acccgagagg tcttctcaac actatcaccc   180
cggagcactt caagagtaaa cttcacatcc cgaccacata caggcaaagt aatggcatta   240
ccgcgagcca ttactcctac gcgcgcaatt aacgaatcca ccatcggggc agctggtgtc   300
gataacgaag tatcttcaac cggttgagta ttgagcgtat gttttggaat aacaggcgca   360
cgcttcatta tctaatctcc cagcgtggtt taatcagacg atcgaaaatt tcattgcaga   420
caggttccca aatagaaaga gcatttctcc aggcaccagt tgaagagcgt tgatcaatgg   480
cctgttcaaa aacagttctc atccggatct gacctttacc aacttcatcc gtttcacgta   540
caacattttt tagaaccatg cttccccagg catcccgaat ttgctcctcc atccacgggg   600
actgagagcc attactattg ctgtatttgg taagcaaaat acgtacatca ggctcgaacc   660
ctttaagatc aacgttcttg agcagatcac gaagcatatc gaaaaactgc agtgcggagg   720
tgtagtcaaa caactcagca ggcgtgggaa caatcagcac atcagcagca catacgacat   780
taatcgtgcc gatacccagg ttaggcgcgc tgtcaataac tatgacatca tagtcatgag   840
caacagtttc aatggccagt cggagcatca ggtgtggatc ggtgggcagt ttaccttcat   900
caaatttgcc cattaactca gtttcaatac ggtgcagagc cagacaggaa ggaataatgt   960
caagccccgg ccagcaagtg ggctttattg cataagtgac atcgtccttt tccccaagat   1020
agaaaggcag gagagtgtct tctgcatgaa tatgaagatc tggtacccat ccgtgataca   1080
ttgaggctgt tccctggggg tcgttacctt ccacgagcaa aacacgtagc cccttcagag   1140
ccagatcctg agcaagatga acagaaactg aggttttgta aac                    1183
```

```
<210> SEQ ID NO 4
<211> LENGTH: 1079
<212> TYPE: DNA
<213> ORGANISM: Sus scrofa

<400> SEQUENCE: 4
gcccccaaga cggcccccatc ggtctaccct ctggcccccct gcggcaggga cgtgtctggc   60
cctaacgtgg ccttgggctg cctggcctca agctacttcc ccgagccagt gaccgtgacc   120
tggaactcgg gcgccctgac cagtggcgtg cacaccttcc catccgtcct gcagccgtca   180
gggctctact cccctcagcag catggtgacc gtgccggcca gcagcctgtc cagcaagagc   240
tacacctgca atgtcaacca cccggccacc accaccaagg tggacaagcg tgttggaata   300
caccagccgc aaacatgtcc catatgccca ggctgtgaag tggccgggcc ctcggtcttc   360
atcttccctc caaaacccaa ggacaccctc atgatctccc agacccccga ggtcacgtgc   420
```

```
gtggtggtgg acgtcagcaa ggagcacgcc gaggtccagt tctcctggta cgtggacggc    480
gtagaggtgc acacggccga gacgagacca aaggaggagc agttcaacag cacctaccgt    540
gtggtcagcg tcctgcccat ccagcaccag gactggctga aggggaagga gttcaagtgc    600
aaggtcaaca acgtagacct cccagccccc atcacgagga ccatctccaa ggctataggg    660
cagagccggg agccgcaggt gtacaccctg cccccacccg ccgaggagct gtccaggagc    720
aaagtcacgc taacctgcct ggtcattggc ttctacccac ctgacatcca tgttgagtgg    780
aagagcaacg gacagccgga gccagagaac acataccgca ccaccccgcc ccagcaggac    840
gtggacggga ccttcttcct gtacagcaaa ctcgcggtgg acaaggcaag atgggaccat    900
ggagacaaat ttgagtgtgc ggtgatgcac gaggctctgc acaaccacta cacccagaag    960
tccatctcca agactcaggg taaatgagcc acccgctgca ccccacgtgc tctcgggtcc   1020
cgcgagctcg cctgagcccc agcgctgtgt acatacgtcc cgggccagca tgaaataaa    1079
```
<210> SEQ ID NO 5
<211> LENGTH: 585
<212> TYPE: DNA
<213> ORGANISM: White spot syndrome virus
<220> FEATURE:
<221> NAME/KEY: modified_base
<222> LOCATION: (546)
<223> OTHER INFORMATION: a, c, g, t, unknown, or other
<220> FEATURE:
<221> NAME/KEY: modified_base
<222> LOCATION: (562)
<223> OTHER INFORMATION: a, c, g, t, unknown, or other

<400> SEQUENCE: 5
```
acatttccca gagatcttca tggacaatgg agcgggatac aaaacggttg ggttttctc     60 ttgtaagtaa gtgtttagac gtatctactt gcataatgag ttttttggtg aatttgtcaa    120
acacttcctg ggcaatcctc ttttcctcct cggttttata ttctgacttg atttcttcag    180
ccacttggtt ggcttgctcc atattcagac cagtaacggt gaacagtttg attgactcca    240
tttctggggt tgttggtatt attggagtaa taatggaagt tgacggtagg accgatgacg    300
agggaatgat gctgtggtgt gagaagtggc catatttata ctcatgcggc tgagtctgga    360 gggggggtt gccatcaatc agccttttta gtcggtatcg gaatcagtgt ggccaattca    420
caaaccatct ctgctcttta ttttgcagac ggtctcaaat acacccttct ggtcttgcaa    480
gatctcctca ataactggtc gatgtcttca atttttatgt aggaagtctt tcatggaaga    540
tatttnctgg ttgttcacaa angcccacag ttccttatat ctggt                    585
```
<210> SEQ ID NO 6
<211> LENGTH: 615
<212> TYPE: DNA
<213> ORGANISM: White spot syndrome virus

<400> SEQUENCE: 6
```
atggatcttt ctttcactct ttcggtcgtg tcggccatcc tcgccatcac tgctgtgatt     60
gctgtattta ttgtgatttt taggtatcac aacactgtga ccaagaccat cgaaacccac    120
acagacaata tcgagacaaa catggatgaa aacctccgca ttcctgtgac tgctgaggtt    180
ggatcaggct acttcaagat gactgatgtg tcctttgaca gcgacacctt gggcaaaatc    240
aagatccgca atggaaagtc tgatgcacag atgaaggaag aagatgcgga tcttgtcatc    300
actcccgtgg agggccgagc actcgaagtg actgtggggc agaatctcac ctttgaggga    360
acattcaagg tgtggaacaa cacatcaaga aagatcaaca tcactggtat gcagatggtg    420
```

-continued

```
ccaaagatta acccatcaaa ggcctttgtc ggtagctcca acacctcctc cttcaccccc      480
gtctctattg atgaggatga agttggcacc tttgtgtgtg gtaccacctt tggcgcacca      540
attgcagcta ccgccggtgg aaatctttc gacatgtacg tgcacgtcac ctactctggc      600
actgagaccg agtaa                                                      615

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctgtctgagc gaaacttcac a                                                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aagtcagcga tcacatcagc t                                                21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccagcaacta gaaggctcac t                                                21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cggttcttgc tgcatcttgc a                                                21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccagaatgag actgatgctg a                                                21

<210> SEQ ID NO 12
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 12
cacgggtgat aatgtctacc a                                              21
```